(12) United States Patent
Weggeman et al.

(10) Patent No.: US 8,124,106 B2
(45) Date of Patent: Feb. 28, 2012

(54) VIRUS PURIFICATION METHODS

(75) Inventors: Miranda Weggeman, Bleiswijk (NL);
Emile J. J. M. van Corven, Utrecht (NL)

(73) Assignee: Crucell Holland B.V., Leiden (NL)

( * ) Notice: Subject to any disclaimer, the term of this patent is extended or adjusted under 35 U.S.C. 154(b) by 120 days.

(21) Appl. No.: 12/220,828

(22) Filed: Jul. 28, 2008

(65) Prior Publication Data

US 2009/0017523 A1 Jan. 15, 2009

Related U.S. Application Data

(62) Division of application No. 10/590,427, filed as application No. PCT/EP2005/050739 on Feb. 21, 2005, now abandoned.

(30) Foreign Application Priority Data

Feb. 23, 2004 (WO) ................ PCT/EP2004/050190

(51) Int. Cl.
*A01N 63/00* (2006.01)
*A61K 39/235* (2006.01)
*C12N 7/02* (2006.01)

(52) U.S. Cl. .................... 424/233.1; 424/93.6; 435/239

(58) Field of Classification Search ........................ None
See application file for complete search history.

(56) References Cited

U.S. PATENT DOCUMENTS

| | | | |
|---|---|---|---|
| 4,435,289 A | 3/1984 | Breslau | |
| 4,579,662 A | 4/1986 | Jonsson et al. | |
| 4,808,315 A | 2/1989 | Manabe et al. | |
| 5,173,418 A | 12/1992 | Molin et al. | |
| 5,559,099 A | 9/1996 | Wickham et al. | |
| 5,789,390 A | 8/1998 | Descamps et al. | |
| 5,837,511 A | 11/1998 | Falck-Pedersen et al. | |
| 5,837,520 A | 11/1998 | Shabram et al. | |
| 5,840,565 A | 11/1998 | Lau | |
| 5,846,782 A | 12/1998 | Wickham et al. | |
| 5,851,806 A | 12/1998 | Kovesdi et al. | |
| 5,891,690 A | 4/1999 | Massie | |
| 5,947,689 A | 9/1999 | Schick | |
| 5,948,410 A | 9/1999 | Van Scharrenburg et al. | |
| 5,965,541 A | 10/1999 | Wickham et al. | |
| 5,981,225 A | 11/1999 | Kochanek et al. | |
| 5,994,106 A | 11/1999 | Kovesdi et al. | |
| 5,994,128 A | 11/1999 | Fallaux et al. | |
| 5,994,134 A | 11/1999 | Giroux et al. | |
| 6,008,036 A | 12/1999 | Fanget et al. | |
| 6,020,191 A | 2/2000 | Scaria et al. | |
| 6,040,174 A | 3/2000 | Imler et al. | |
| 6,113,913 A | 9/2000 | Brough et al. | |
| 6,120,820 A | 9/2000 | Brody et al. | |
| 6,143,548 A * | 11/2000 | O'Riordan et al. | 435/239 |
| 6,146,873 A | 11/2000 | Kistner et al. | |
| 6,168,941 B1 | 1/2001 | Liu et al. | |
| 6,168,944 B1 | 1/2001 | Condon et al. | |
| 6,194,191 B1 * | 2/2001 | Zhang et al. | 435/239 |
| 6,261,823 B1 | 7/2001 | Tang et al. | |
| 6,309,650 B1 | 10/2001 | Kim et al. | |
| 6,342,384 B1 | 1/2002 | Chung et al. | |
| 6,365,395 B1 | 4/2002 | Antoniou | |
| 6,451,256 B1 | 9/2002 | Sene | |
| 6,485,958 B2 | 11/2002 | Blanche et al. | |
| 6,492,169 B1 | 12/2002 | Vogels et al. | |
| 6,537,793 B2 | 3/2003 | Blanche et al. | |
| 6,586,226 B2 | 7/2003 | Carrion et al. | |
| 2001/0036657 A1 * | 11/2001 | Tang et al. | 435/239 |
| 2002/0177215 A1 | 11/2002 | Zhang et al. | |
| 2002/0182723 A1 | 12/2002 | Cho et al. | |
| 2003/0171560 A1 | 9/2003 | Peters | |
| 2005/0003507 A1 * | 1/2005 | Kostel et al. | 435/239 |
| 2005/0153420 A1 * | 7/2005 | Konz, Jr. et al. | 435/239 |

FOREIGN PATENT DOCUMENTS

| | | |
|---|---|---|
| EP | 1 230 354 B1 | 8/2002 |
| WO | WO 96/00237 | 1/1996 |
| WO | WO 96/26281 | 8/1996 |
| WO | WO 97/08298 | 3/1997 |
| WO | WO 98/22588 | 5/1998 |
| WO | WO 98/33886 | 8/1998 |
| WO | WO 98/39411 | 9/1998 |
| WO | WO 99/12568 | 3/1999 |
| WO | WO 99/41416 | 8/1999 |
| WO | WO 00/03029 | 1/2000 |
| WO | WO 00/29024 | 8/2000 |
| WO | WO 00/50573 | 8/2000 |

(Continued)

OTHER PUBLICATIONS

Hugyne et al., Purification of a Type 5 Recombinant Adenovirus Encoding Human p53 by Column Chromatography, 1995, Human Gene Therapy, vol. 6, No. 11, pp. 1403-1416, (1995).*
A product catalogue of the Milliport® ProFluxTM M12 system, 2000, Millipore Corporation.
Crespo et al., Use of fluorescence labeling to monitor protein fractionation by ultrafiltration under controlled permeate flux, Journal of Membrane Science, pp. 209-230, vol. 155, 1999.
Decloux et al., Importance of the control mode in ultrafiltration: case of raw cane sugar remelt, Journal of Food Engineering, 2000, pp. 119-126, vol. 44.
Flickinger et al., Bioprocess Technology: Fermentation, Biocatalysis, and Bioseparation, 1999, vol. 4, publisher: John Wiley & Sons, Inc., pp. 2197-2214.
Huyghe et al., Purification of a Type 5 Recombinant Adenovirus Encoding Human p53 by Column Chromatography, Human Gene Therapy, 1995, pp. 1403-1416, vol. 6.

(Continued)

*Primary Examiner* — Benjamin P Blumel
(74) *Attorney, Agent, or Firm* — TraskBritt

(57) ABSTRACT

Provided is a method for purifying a virus from a host cell, the method comprising: a) culturing host cells, b) infecting the host cells with a virus, c) treating the cell culture with nuclease, and d) lysing the host cells to provide a lysate comprising the virus. The virus may be recombinant adenovirus. Further provided are methods for purifying a recombinant virus expressing a heterologous protein capable of binding nucleic acid, comprising: a) culturing host cells, b) infecting the host cells with recombinant virus, c) lysing the host cells to provide a lysate comprising the recombinant virus, d) subjecting the recombinant virus to anion exchange chromatography and size exclusion chromatography, wherein the virus-containing mixture is buffer exchanged at least once with a solution comprising at least 2 M NaCl, or another salt providing an equivalent ionic strength.

6 Claims, 12 Drawing Sheets

FOREIGN PATENT DOCUMENTS

Figure 1:
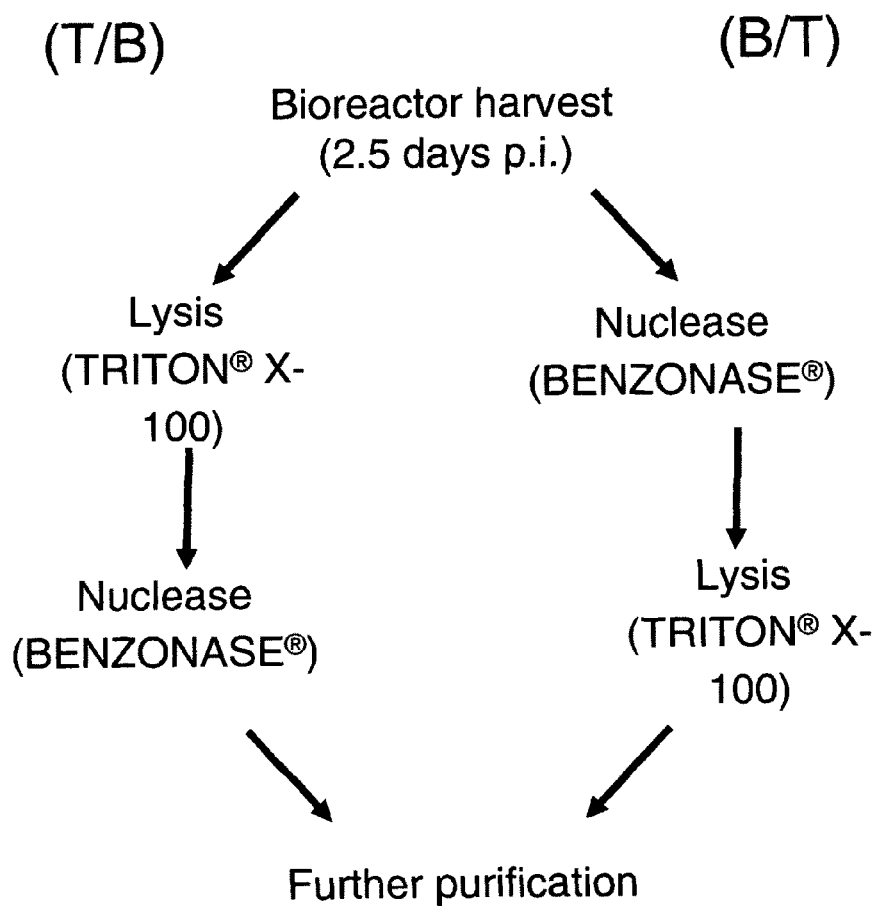

| | | |
|---|---|---|
| WO | WO 00/70071 | 11/2000 |
| WO | WO 01/36615 | 5/2001 |
| WO | WO 01/38362 | 5/2001 |
| WO | WO 01/66137 A1 | 9/2001 |
| WO | WO 01/77304 | 10/2001 |
| WO | WO 02/22080 | 3/2002 |
| WO | WO 02/44348 | 6/2002 |
| WO | WO 02/067861 A2 | 9/2002 |
| WO | WO 02/070673 | 9/2002 |
| WO | WO 03/028632 | 4/2003 |
| WO | WO 03/049763 | 6/2003 |
| WO | WO 03/078592 | 9/2003 |
| WO | WO 03/084479 | 10/2003 |
| WO | WO 03/097797 * | 11/2003 |
| WO | WO 03/104467 | 12/2003 |
| WO | WO 2004/001032 | 12/2003 |
| WO | WO 2004/092348 A2 | 10/2004 |
| WO | WO 2005/080556 | 9/2005 |

OTHER PUBLICATIONS

Membrane Separations in Biotechnology, edited by W.K. Wang, $2^{nd}$ Edition (Apr. 2001), publisher: Marcel Dekker Inc., pp. 129-133, 207.

Notice of opposition to a European patent for Patent No. 1 869 171 (date of mention of grant in the European Patent Bulletin is Oct. 29, 2008.

PCT International Preliminary Report, PCT/EP2006/003722, dated Jul. 9, 2007.

PCT International Search Report, PCT/EP2006/003722, dated Jun. 30, 2006.

Printout from the website of Millipore Corporation of ordering informations for the Pellicon® system (website: www.millipore.com/catalogue/module/C613 dated Sep. 7, 2009.

Protein concentration and diafiltration by tangential flow filtration, a technical brief from Millipore Corporation, 2003, Millipore Corporation, Billenco, MA 01821, USA.

Senica et al., Pilot plant unit for a cross-flow microfiltration and ultrafiltration of fermentation broths, Acta Chem. Slov. 1999, pp. 587-602, vol. 46, No. 4.

U.S. Appl. No. 11/909,955, filed Sep. 27, 2007, Miranda Weggeman, Virus Purification Using Ultrafiltration.

PCT International Preliminary Report on Patentability, PCT/EP2005/050439, dated Jul. 18, 2006.

PCT International Search Report, PCT/EP 2005/050439, dated Oct. 27, 2005.

Green et al., "A new Scalable Method for the Purification of Recombinant Adenovirus Vectors," Human Gene Therapy, Nov. 1, 2002, pp. 1921-1934, vol. 13.

Drittanti et al., "Optimised helper virus-free production of high-quality adeno-associated virus vectors," The Journal of Gene Medicine, 2001, pp. 59-71, vol. 3.

Sullivan et al., "Development of a preventive vaccine for Ebola virus infection in primates," Nature, Nov. 30, 2000, pp. 609-609, vol. 408.

Cook et al., "Purification of Virus-like Particles of Recombinant Human Papillomavirus Type 11 Major Capsid Protein L1 from *Saccharomyces cerevisiae*," Protein Expression and Purification, 1999, vol. 17, pp. 477-484.

Notice of Opposition by Sartorius, Mar. 31, 2010.

Mustang Q Capsules and Cartridges, Technical Information, 2000.

Yang et al., Purification of a Large Protein Using Ion-Exchange Membranes, Ind. Eng. Chem. Res., 2002, pp. 1597-602, vol. 41.

Cooper, Terrance G., Biochemische Arbeitsmethoden, 1981, pp. 140-144; similar English version also attached—Cooper, Terrance G., The Tools of Biochemistry, 1977, pp. 151-155, 167-168.

* cited by examiner

VIRUS PURIFICATION METHODS

CROSS-REFERENCE TO RELATED APPLICATIONS

This application is a divisional of application Ser. No. 10/590,427, filed Aug. 23, 2006, pending, which is the national phase entry of PCT International Patent Application No. PCT/EP2005/050739, filed on Feb. 21, 2005, designating the United States of America, and published, in English, as PCT International Publication No. WO 2005/080556 on Sep. 1, 2005, which claims priority to PCT/EP04/050190 filed Feb. 23, 2004, the contents of the entirety of each of which are incorporated herein by this reference.

TECHNICAL FIELD

The invention relates generally to biotechnology, and more particularly belongs to the field of purification of viruses, more in particular, recombinant adenovirus from host cells.

BACKGROUND

Viruses, either those occurring in nature or recombinant versions thereof, are used for vaccination and in the field of gene therapy. It is possible for many viruses or virus-like particles to safely and efficiently propagate these in host cells (see, for instance, WO 01/38362, which describes the propagation of various viruses in host cells being E1-immortalized retina cells). Recombinant adenoviruses are a preferred class of viral vectors for use in gene therapy and for vaccination purposes. Such recombinant adenoviruses are usually deficient in at least the E1 region, and are propagated in complementing cells providing the E1-region, such as 293 cells, or E1-immortalized retina cells, such as PER.C6® cells (see, for instance, U.S. Pat. No. 5,994,128, the contents of the entirety of which are incorporated herein by this reference).

After propagation of the viruses in the host cells, for virtually all applications it is necessary to purify the viruses from the host cells before further use.

International patent application WO 98/22588, the contents of the entirety of each of which are incorporated herein by this reference, describes methods for the production and purification of adenoviral vectors. The methods comprise growing host cells, infecting the host cells with adenovirus, harvesting and lysing the host cells, concentrating the crude lysate, exchanging the buffer of the crude lysate, treating the lysate with nuclease, and further purifying the virus using chromatography.

Several other publications describe the purification of viruses from host cells, mostly concentrating on the use of specific chromatographic matrices for purification of the virus from a host cell lysate, see, e.g., U.S. Pat. Nos. 6,008,036, 6,586,226, 5,837,520, 6,261,823, 6,537,793, and international patent applications WO 00/50573, WO 02/44348 and WO 03/078592, the contents of the entirety of each of which are incorporated herein by this reference.

Most of the described methods apply a nuclease treatment step to degrade DNA impurities. Despite the description of several processes regarding different chromatography matrices, a need remains for alternative, and preferably improved, methods for virus purification from host cell cultures.

SUMMARY OF THE INVENTION

Provided are methods for the purification of a virus from a host cell, the method comprising the steps of: a) culturing host cells that are infected with a virus, b) adding nuclease to the cell culture, and c) lysing the host cells to provide a lysate comprising the virus. In certain embodiments, the method further comprises: d) clarification of the lysate. In still other embodiments, the method further comprises: e) further purifying the adenovirus, preferably with at least one chromatography step. The most important difference with the methods hitherto disclosed is that in those methods, a nuclease is applied only after lysing the cells or at a later stage in the purification process.

According to the disclosure, a nuclease is added before lysing the cells. As disclosed herein, it has now been unexpectedly found that this results in an improvement over the processes wherein nuclease is added only after the cells have been lysed. In certain methods, the purified virus batch resulting from this process contains less host cell DNA than with the method wherein the lysing of cells precedes the nuclease addition. In certain embodiments, the virus is a recombinant adenovirus. In certain embodiments, the nuclease used in step b) is BENZONASE®.

In certain embodiments, the step of lysing the host cells (step c) is performed with a detergent, which in one embodiment thereof is TRITON® X-100. In certain embodiments, the clarification of the lysate (step d) comprises depth filtration and membrane filtration. In an embodiment thereof, membrane filtration is performed using a combination of filters having a pore size of 0.8 μm and 0.45 μm, such as a combination filter comprising two asymmetric polyethersulfone membranes with pore sizes of 0.8 and 0.45 μm, such as a SARTOPORE® 2 combination filter. In certain embodiments, the clarified lysate (resulting from step d) is subjected to ultrafiltration and/or diafiltration. In an embodiment thereof, the diafiltration results in buffer exchange against a solution comprising 0.8-2.0 M NaCl, or another salt providing an equivalent ionic strength.

In certain embodiments, further purification of the virus (step e) comprises anion exchange chromatography. In another embodiment, further purification of the virus (step e) comprises a size exclusion chromatography step, preferably in group separation mode. In another embodiment, step e) comprises both anion exchange chromatography and size exclusion chromatography. In certain embodiments, the clarified lysate and further purified virus (from step d onwards) are in buffers that are free of detergent, magnesium chloride and sucrose.

In another aspect, provided is a batch of recombinant adenovirus comprising a transgene chosen from the group consisting of: an Ebola virus nucleoprotein, an Ebola virus glycoprotein, a *Plasmodium falciparum circumsporozoite* gene, and measles virus hemagglutinin, the batch characterized in that it contains less than 0.1 ng host cell DNA per 1E11 viral particles.

Further provided are methods for the production of a virus comprising a nucleic acid sequence coding for a nucleic acid binding protein, comprising the steps of: a) culturing host cells that have been infected with virus, b) subjecting the culture of host cells and the virus therein produced to lysis of the host cells to provide a lysate comprising the virus, c) subjecting the virus to anion exchange chromatography, characterized in that after anion exchange chromatography, the virus-containing mixture is buffer exchanged with a solution comprising at least 1 M NaCl, or another salt providing an equivalent ionic strength. Preferably, the solution comprises at least 1.5 M NaCl, more preferably at least 2 M NaCl, still more preferably at least 3 M NaCl, and most preferably about 5 M NaCl or another salt providing an equivalent ionic strength. Preferably, the virus is further purified using filtration through a hydrophilic filter, preferably with a pore size not larger than 1.2 µm and/or by size exclusion chromatography. The virus preferably is a recombinant virus, more preferably a recombinant adenovirus. The nucleic acid binding protein may be a nuclear protein, such as a nucleoprotein of a hemorrhagic fever virus, such as Ebola, Marburg or Lassa virus.

BRIEF DESCRIPTION OF THE SEVERAL VIEWS OF THE DRAWINGS

FIG. 1. Scheme of the known method of harvesting the cells (T/B) versus the method according to the invention (B/T), see example 1. T: TRITON®; B: BENZONASE®; p.i.: post infection.

FIG. 2. Host cell protein removal at clarification after T/B vs. B/T process (see, FIG. 1 for scheme). A silver-stained SDS-PAGE (4-12% bis-tris NuPAGE, Invitrogen) analysis of in-process samples of five separate purifications is shown (see, example 1 and Table 1 for samples). Panel 2 is from a T/B harvest, wherein lysis preceded nuclease addition; panels 3-7 are from a B/T harvest, wherein nuclease was added before lysis. The harvest (lanes 1) was clarified by a 0.5 μm Clarigard filter (lanes 2), followed by a 0.8/0.45 μm SARTOPORE® 2 filter (lanes 3). M: marker, $M_w$ in kD is shown alongside.

FIG. 3. Diafiltration with high salt removes histones during process (see, example 2). A silver-stained SDS-PAGE is shown. A. Permeate. Samples: Lane 1, initial permeate; Lane 2, after 4× concentration; Lane 3, first DFV 0.3 M NaCl; Lane 4, third DFV 0.6 M NaCl; Lane 5, fourth DFV 0.6 M NaCl; Lane 6, fifth DFV 1.0 M NaCl; Lane 7, sixth DFV 1.0 M NaCl; Lane 8, seventh DFV 0.3 M NaCl; Lane 9, ninth DFV 0.3 M NaCl; Lane M, marker, $M_w$ in kD is shown alongside. B. Retentate. Samples: Lane 1, start sample; Lane 2, after 4× concentration; Lane 3, first DFV 0.3 M NaCl; Lane 4, second DFV 0.6 M NaCl; Lane 5, sixth DFV 0.6 M NaCl; Lane 6, seventh DFV 1.0 M NaCl; Lane 7, eighth DFV 1.0 M NaCl; Lane 8, ninth DFV 0.3 M NaCl; Lane 9, ninth DFV millex (0.22 μm filtrate of sample 8); Lane M, marker, $M_w$ in kD is shown alongside.

FIG. 4. Scheme of a preferred process according to the invention (see, example 1).

FIG. 5. Removal of Ebola nucleoprotein (NP) from recombinant virus preparations (see, example 3, experiment 3.1 for details). A silver-stained SDS-PAGE (4-12% bis-tris NuPAGE, Invitrogen) is shown. Lane A, starting material; Lane B, incubation with 1% Tween 20®; Lane C, incubation with 2.5 M NaCl. The arrow denotes NP.

FIG. 6. Experiment for removal of Ebola nucleoprotein from recombinant virus preparations (see, example 3, experiment 3.3 for details).

FIG. 7. Non-reduced SDS-PAGE (panel 1) and Western blot (panel 2) analysis of removal of Ebola nucleoprotein (NP) from recombinant virus preparations (see, example 3, experiment 3.3 for details). Lanes A, B, C contain product A, B and C, respectively (see, FIG. 6 and experiment 3.3). For the Western blot analysis, an antibody recognizing NP was used. The arrows denote NP.

FIG. 8. RP-HPLC analysis of removal of Ebola nucleoprotein (NP) from recombinant virus. Products A, B and C were analyzed. For details, see example 3, experiment 3.3. The vertical axis is in AU ($\times 10^{-3}$). Under the horizontal axis (elution time), arrow 1 indicates the peak of hexon protein and arrow 2 indicates peak of NP.

FIG. 9. SDS-PAGE (panel A) and Western blot (panel B) showing the removal of Ebola nucleoprotein (NP) from recombinant virus preparations using high salt and filtration. After anion exchange chromatography, the sample was buffer exchanged with a solution comprising 5 M NaCl. The sample was directly filtered through a 0.45 μm Millipac 20 filter (Millipore). Lane 1, before filtration; Lane 2, after filtration. For the Western blot, an antibody recognizing NP was used. The arrow denotes NP.

FIG. 10. Chromatogram of Ad35 TFF retentate (example 6) loaded on a Q-XL column (panel A) and on a charged filter (panel B). The circle in panel B indicates the extra peak, which is only separated from the virus peak using the charged filter.

FIG. 11. Disc centrifugation analysis of two fractions of the charged filter chromatogram. Panel A shows the sedimentation profile of the Ad35 virus peak and panel B shows the sedimentation profile of the extra peak (circled in FIG. 10).

FIG. 12. SDS-PAGE analysis of chromatography fractions Ad35 (see, example 6). 4-12% bis-tris gel, stained with silver. Gel A shows the fractions of the charged filter run: 1. marker; 2. start material; 3. flow through; 4. peak 1 (circled in FIG. 10); 5. Ad35 peak. Gel B shows the fractions of the Q-XL run: Lane 1, start material; Lane 2, flow through; Lane 3, Ad35 peak.

DETAILED DESCRIPTION OF THE INVENTION

Host Cells

A host cell according to the invention can be any host cell wherein a desired virus can be propagated. For example, the propagation of recombinant adenovirus vectors is done in host cells that complement deficiencies in the adenovirus. Such host cells preferably have in their genome at least an adenovirus E1 sequence and thereby are capable of complementing recombinant adenoviruses with a deletion in the E1 region. Further, the adenovirus may have a deletion in the E3 region, which is dispensable from the Ad genome and, hence, such a deletion does not have to be complemented. Any E1-complementing host cell can be used, such as human retina cells immortalized by E1, e.g., 911 (see, U.S. Pat. No. 5,994,128), E1-transformed amniocytes (see, EP Patent 1230354), E1-transformed A549 cells (see, e.g., WO 98/39411, U.S. Pat. No. 5,891,690), GH329:HeLa (Gao et al., 2000, *Human Gene Therapy* 11: 213-219), 293, and the like. Preferably, PER.C6® cells (U.S. Pat. No. 5,994,128), or cells derived therefrom, are used as host cells, as they are suitable for the propagation of various different viruses (see, e.g., WO 01/38362) including, but not limited to, recombinant adenoviruses. The contents of the entirety of each of these patent references are incorporated herein by this reference.

Further, cell lines and methods for the propagation of recombinant adenoviral vectors have, for instance, been disclosed in U.S. Pat. No. 6,492,169 and in WO 03/104467, the contents of the entirety of each of which are incorporated herein by this reference.

Examples of other useful mammalian cell lines that may be used directly as host cells for propagating viruses or converted into complementing host cells for replication-deficient virus are Vero and HeLa cells and cell lines of Chinese hamster ovary, W138, BHK, COS-7, HepG2, 3T3, RIN and MDCK cells, as known to the person skilled in the art.

Host cells according to the invention are cultured to increase cell and virus numbers and/or virus titers. Culturing a cell is done to enable it to metabolize, grow, divide and/or produce virus of interest according to the invention. This can be accomplished by methods well known to persons skilled in the art and includes, but is not limited to, providing nutrients for the cell, for instance, in the appropriate culture media. The methods may comprise growth adhering to surfaces, growth in suspension, or combinations thereof. Culturing can be done, for instance, in dishes, roller bottles or in bioreactors, using batch, fed-batch, continuous systems, hollow fiber, and the like. In order to achieve large-scale (continuous) production of virus through cell culture, it is preferred in the art to have cells capable of growing in suspension, and it is preferred to have cells capable of being cultured in the absence of animal- or human-derived serum or animal- or human-derived serum components. Suitable conditions for culturing cells are known (see, e.g., *Tissue Culture*, Academic Press, Kruse and Paterson, editors (1973), and R. I. Freshney, Culture of animal cells: A manual of basic technique, fourth edition (Wiley-Liss Inc., 2000, ISBN 0-471-34889-9).

The invention comprises subjecting cultured host cells that are infected with virus to lysis. Culturing host cells and infecting them with a virus is well known to the person skilled in the art. Infecting of host cells can, for instance, simply be accomplished by exposing the virus to the appropriate host cell under physiological conditions, permitting uptake of the virus. For certain viruses, it is not even necessary to start with virus per se, as nucleic acid sequences may be used to reconstitute the virus in the cultured cells.

Several aspects of, and systems suitable for, culturing host cells for adenovirus production can also be found in WO 98/22588, p. 11-28. Methods for culturing cells and propagating viruses in host cells have also been disclosed in, for example, U.S. Pat. Nos. 6,168,944, 5,994,134, 6,342,384, 6,168,941, 5,948,410, 5,840,565, 5,789,390, 6,309,650, 6,146,873 and international patent applications WO 01/38362, WO 01/77304 and WO 03/084479, the contents of the entirety of each of which are incorporated herein by this reference.

Viruses

The methods of the instant invention are amenable to a wide range of viruses including, but not limited to, adenoviruses, pox viruses, irido viruses, herpes viruses, papova viruses, paramyxoviruses, orthomyxoviruses (such as influenza), retroviruses, adeno-associated virus, vaccinia virus, rotaviruses, etc., adenoviruses being particularly preferred. The viruses are preferably recombinant viruses, but can include clinical isolates, attenuated vaccine strains, and so on. In certain embodiments, the invention is used for concentrating recombinant viruses, preferably adenoviruses, carrying a heterologous transgene for use in gene therapy or for vaccination purposes. For purposes of illustration only, the invention will be described in more detail for recombinant adenovirus, but is in no way limited thereto.

Adenoviruses

Preferably, the adenoviral vector is deficient in at least one essential gene function of the E1 region, e.g., the E1a region and/or the E1b region, of the adenoviral genome that is required for viral replication. In certain embodiments, the vector is deficient in at least one essential gene function of the E1 region and at least part of the nonessential E3 region (e.g., an XbaI deletion of the E3 region). The adenoviral vector can be "multiply deficient," meaning that the adenoviral vector is deficient in one or more essential gene functions in each of two or more regions of the adenoviral genome. For example, the aforementioned E1-deficient or E1-, E3-deficient adenoviral vectors can be further deficient in at least one essential gene of the E4 region and/or at least one essential gene of the E2 region (e.g., the E2A region and/or E2B region). Adenoviral vectors deleted of the entire E4 region can elicit lower host immune responses. Examples of suitable adenoviral vectors include adenoviral vectors that lack (a) all or part of the E1 region and all or part of the E2 region, (b) all or part of the E1 region, all or part of the E2 region, and all or part of the E3 region, (c) all or part of the E1 region, all or part of the E2 region, all or part of the E3 region, and all or part of the E4 region, (d) at least part of the E1a region, at least part of the E1b region, at least part of the E2a region, and at least part of the E3 region, (e) at least part of the E1 region, at least part of the E3 region, and at least part of the E4 region, and (f) all essential adenoviral gene products (e.g., adenoviral amplicons comprising ITRs and the packaging signal only). In the case of deletions of essential regions from the adenovirus genome, the functions encoded by these regions have to be provided in trans, preferably by the host cell, i.e., when parts or all of E1, E2 and/or E4 regions are deleted from the adenovirus, these have to be present in the host cell, for instance, integrated in the genome or in the form of so-called helper adenovirus or helper plasmids.

The replication-deficient adenoviral vector can be generated by using any species, strain, subtype, or mixture of species, strains, or subtypes, of an adenovirus or a chimeric adenovirus as the source of vector DNA (see, for instance, WO 96/26281, WO 00/03029), which, for instance, may provide the adenoviral vector with the capability of infecting certain desired cell types. The adenoviral vector can be any adenoviral vector capable of growth in a cell, which is in some significant part (although not necessarily substantially) derived from or based upon the genome of an adenovirus. The adenoviral vector may comprise an adenoviral genome of a wild-type adenovirus of group C, especially of serotype 5 (i.e., Ad5) or Ad2. The adenoviral vector may also comprise an adenoviral genome or at least a fiber protein derived from an adenovirus of group B, for instance Ad11, Ad35, Ad51, etc. (see, e.g. WO 00/70071), which embodiments have the advantage that less neutralizing antibodies against these serotypes are encountered in the population, and confer the possibility of targeting other cell types, since the tropism of these adenoviral vectors differs from those derived from Ad5. Any other serotype can also be applied. It is possible to propagate adenoviral vectors of numerous different serotypes on specific host cells, using methods such as, for instance, disclosed in U.S. Pat. No. 6,492,169 or in WO 03/104467, and references therein. Adenoviral vectors, methods for construction thereof and methods for propagating thereof, are well known in the art and are described in, for example, U.S. Pat. Nos. 5,559,099, 5,837,511, 5,846,782, 5,851,806, 5,994,106, 5,994,128, 5,965,541, 5,981,225, 6,040,174, 6,020,191, and 6,113,913, and Thomas Shenk, "Adenoviridae and their Replication," M. S. Horwitz, "Adenoviruses," Chapters 67 and 68, respectively, in *Virology*, B. N. Fields et al., eds., 3d ed., Raven Press, Ltd., New York (1996), and other references mentioned herein, the contents of the entirety of each of which are incorporated herein by this reference.

The construction of adenoviral vectors is well understood in the art and involves the use of standard molecular biological techniques, such as those described in, for example, Sambrook et al., *Molecular Cloning, a Laboratory Manual,* 2d ed., Cold Spring Harbor Press, Cold Spring Harbor, N.Y. (1989); Watson et al., *Recombinant DNA,* 2d ed., Scientific American Books (1992); and Ausubel et al., *Current Protocols in Molecular Biology*, Wiley Interscience Publishers, N.Y. (1995), and other references mentioned herein.

Transgenes

In certain embodiments, the virus according to the invention is a wild-type virus, or a mutant or part thereof that is still infectious in host cells according to the invention.

In another embodiment, the virus is a recombinant virus comprising heterologous information, which may be used in a therapeutic setting for gene therapy purposes, or as an antigen for vaccination purposes. This is an embodiment using, for instance, adenoviral vectors. The heterologous information is referred to as "transgene." The methods according to the invention are applicable with a virus, preferably adenovirus, comprising any transgene, and hence, the nature of the transgene is in itself not material to the invention.

Several possible transgenes have, for instance, been described in WO 98/22588, p. 42-49. Transgenes that may be present in a virus according to the invention may, for instance, be therapeutic genes, such as tumor suppressor genes, including but not limited to p53, p16, APC, DCC, NF-1, WT-1, p21, BRCA1, BRCA2, and the like; enzymes, such as cytosine deaminase, HGPRT, glucocerebrosidase, HSV thymidine kinase or human thymidine kinase, etc.; hormones, such as growth hormone, prolactin, erythropoietin, chorionic gonadotropin, thyroid-stimulating hormone, leptin, ACTH, angiotensin, insulin, glucagon, somatostatin, calcitonin, vasopressin, and the like; interleukins and cytokines, such as IL-1, IL-3, IL-12, G-CSF, GM-CSF, TNF, and the like; replacement genes lacking or mutated in specific disorders, such as ADA, factor IX, CFTR, etc.; other therapeutic genes such as angiogenesis inhibitors, cell cycle inhibitors and the like; antisense constructs to inhibit expression of, for instance, oncogenes, such as ras, myc, jun, bcl, abl, and the like; as well as antigens for vaccines such as viral antigens, for instance, derived from a picornavirus, coronavirus, togavirus, flavivirus, rhabdovirus, paramyxovirus, orthomyxovirus, poxvirus, hepadnavirus, reovirus, retrovirus, herpesvirus, and the like, for instance, more specifically, antigens from influenza (with as potential antigens, for instance, HA and/or NA), hepatitis B (with as potential antigen, hepatitis B surface antigen), West Nile Virus, rabies, SARS-CoV, herpes simplex virus 1 and 2, measles, small pox, polio, HIV (with antigens, e.g., HIV-1-derived gag, env, nef, or modifications thereof including codon-optimized versions, see, for instance, WO 02/22080), Ebola, Marburg, Lassa virus; or bacterial antigens, fungal antigens, parasitic (including trypanosomes, tapeworms, roundworms, helminths, malaria, etc.) antigens, and the like.

The person skilled in the art will choose the gene of interest that is useful in the envisaged therapeutic setting, be it in gene therapy and/or in vaccination, and is not confined to the list above. Control regions for the transgene are preferably present in recombinant viral vectors aimed at expression of the transgene, for instance, including a promoter and a polyadenylation signal. These are all aspects well known to the person skilled in the art, and need not be further elaborated here. Several control regions are discussed in WO 98/22588, p. 49-55.

Some adenoviruses used in the invention are further discussed in the examples.

Lysing Host Cells

After infection of an adenovirus, the virus replicates inside the cell and is thereby amplified. Adenovirus infection results finally in the lysis of the cells being infected. The lytic characteristic of adenovirus, therefore, permits two different modes of virus production. The first mode is harvesting virus prior to cell lysis, employing external factors to lyse the cells. The second mode is harvesting virus supernatant after (almost) complete cell lysis by the produced virus (see, e.g., U.S. Pat. No. 6,485,958, describing the harvesting of adenovirus without lysis of the host cells by an external factor). For the latter mode, longer incubation times are required in order to achieve complete cell lysis and, hence, high yields of virus. Furthermore, the gradual spill of the host cell contents into the medium may be detrimental to the integrity and yield of the obtained viruses. Hence, it is preferred to employ external factors to actively lyse the cells, according to the invention.

Methods that can be used for active cell lysis are known to the person skilled in the art and have, for instance, been discussed in WO 98/22588, p. 28-35. Useful methods in this respect are, for example, freeze-thaw, solid shear, hypertonic and/or hypotonic lysis, liquid shear, sonication, high-pressure extrusion, detergent lysis, combinations of the above, and the like. In one embodiment of the invention, the cells are lysed using at least one detergent. Use of a detergent for lysis has the advantage that it is an easy method and that it is easily scalable. In another embodiment, the cells are lysed by shear using hollow fiber ultrafiltration, such as described in WO 03/084479.

Detergents

Detergents that can be used according to the invention, and the way they are employed, are generally known to the person skilled in the art. Several examples are, for instance, discussed in WO 98/22588, p. 29-33.

Detergents, as used herein, can include anionic, cationic, zwitterionic, and nonionic detergents. Exemplary detergents include, but are not limited to, taurocholate, deoxycholate, taurodeoxycholate, cetylpyridium, benzalkonium chloride, ZWITTERGENT-3-14®, CHAPS (3-[3-Cholamidopropyl) dimethylammonionl]-1-propanesulfonate hydrate, Aldrich), Big CHAP, Deoxy Big CHAP, TRITON® X-100, TRITON® X-114, C12E8, Octyl-B-D-Glucopyranoside, PLURONIC-F68®, TWEEN 20®, TWEEN 80® (CALBIOCHEM® Biochemicals), THESIT®, NP-40®, BRIJ-58®, octyl glucoside, and the like. The concentration of the detergent may be varied, for instance, within the range of about 0.1%-5% (w/w). In certain embodiments, the detergent is present in the lysis solution at a concentration of about 1% (w/w). In some pilot experiments of the inventors, use of TRITON® resulted in less viscous solutions than some other detergents tested (TWEEN 20®, TWEEN 80®, deoxycholate). In one embodiment of the invention, the detergent used is TRITON® X-100.

Nuclease

The invention employs nuclease to remove contaminating, i.e., mostly host cell, nucleic acids. Exemplary nucleases suitable for use in the invention include BENZONASE®, PULMOZYME®, or any other DNase and/or RNase commonly used within the art. In preferred embodiments of the invention, the nuclease is BENZONASE®, which rapidly hydrolyzes nucleic acids by hydrolyzing internal phosphodiester bonds between specific nucleotides, thereby reducing the viscosity of the cell lysate. BENZONASE® can be commercially obtained from Merck KGaA (code W214950).

The concentration in which the nuclease is employed is preferably within the range of 1-100 units/ml.

According to the invention, the nuclease is employed before the cells are lysed. It may be added just seconds prior to (or virtually concomitant with) the lysis step, but preferably, the nuclease is added to the culture at least one minute before the lysis step. The cell culture with the added nuclease can then be incubated above process temperature, e.g., around 40° C., or at the culturing temperature (e.g., between about 35° C. to about 37° C.), or at room temperature (around 20° C.) or lower (e.g., around 0° C.), wherein, in general, longer incubation times are required at lower temperatures to achieve the same result (see, BENZONASE® brochure Merck KGaA code W 214950). As a non-limiting example, the incubation can, for instance, be performed at about 37° C. for about 10 minutes, after which the cells are lysed. The nuclease can, and preferably will, still actively degrade nucleic acid after the lysis step, and in certain embodiments according to the invention, the incubation of the cells with endonuclease after lysis is prolonged for about 50 minutes (resulting in a total time of the nuclease treatment of about one hour, although this time may effectively be still longer, because it is likely that the nuclease will still be functional until it is removed in subsequent purification steps). This is considerably shorter than the overnight incubation disclosed in WO 98/22588. Longer incubation, such as, for instance, two hours or overnight or longer incubation (in BENZO-NASE® brochure Merck KGaA code W 214950, data for up to 30-hours incubation are provided) is also possible according to the methods of the invention, but is not required to obtain acceptable results.

The "lysis step" (i.e., subjecting the cells containing the virus produced therein to lysis) as used in these embodiments, is meant to be a lysis step employing external factors (see, under "lysing host cells" above), such as a detergent. During the culturing of the cells wherein the adenovirus is propagated, some cells may already lyse because of the virus in absence of any external lysis factors. Hence, in certain embodiments, such lysis in the absence of external factors has occurred in less than 50%, preferably less than 40%, more preferably less than 30%, still more preferably less than 20% of the host cells, when nuclease treatment is started, i.e., preferably nuclease is added when the cells have a viability of at least 50%, 60%, 70%, 80%, respectively.

Although not preferred (see, above), methods that are dependent on lysis of the host cells in the absence of external factors can be used. Processes involving "spontaneous" lysis have been described, wherein the use of BENZONASE® is discouraged (see, U.S. Pat. No. 6,485,958). However, according to the present inventors it will also be beneficial in such systems to add nuclease during the later stages of the culture, i.e., preferably when the host cells wherein the virus is propagated still have a viability of at least 5%, more preferably at least 10%, still more preferably at least 20% (i.e., when less than 95%, 90%, 80% of the cells are lysed, respectively). This will likely improve the process in quality of the obtained virus when this step would be employed. It is, therefore, another aspect of the invention to provide a method for the purification of a virus that is capable of lysing host cells from host cells, the method comprising the steps of: a) culturing host cells comprising a virus capable of lysing the host cells, b) harvesting virus following their release into culture fluid without lysis of the host cells by an external factor, characterized in that a nuclease is added to the culture before 95% of the host cells have been lysed. In certain embodiments, the nuclease is added to the culture before 90%, preferably 80%, of the host cells have been lysed. The finding of the optimal moment (i.e., corresponding to the optimal percentage of cells that have been lysed) to add the nuclease in these aspects of the invention will depend on the amount of nuclease added and the decrease in specific activity of the nuclease during incubation, and can be empirically found by the person skilled in the art, now the advantage of the addition of nuclease to the culture per se has been disclosed by the present inventors. The obtained lysate according to this aspect of the invention can be further purified employing methods and steps as discussed herein, such as filtration and chromatography.

International patent application WO 03/097797 describes alternative methods for purifying adenovirus particles from cell lysates, comprising the addition of a selective precipitation agent to precipitate impurity DNA. Although it is stated therein that a nuclease step is not required when that method is used, such a step in a later stage of the procedure is used for robustness. The method according to the invention, including the step of adding a nuclease prior to host cell lysis, might suitably be combined with the addition of a selective precipitation agent after lysis, thereby making a step of nuclease addition later in the process (as preferred in WO 03/097797) potentially superfluous.

International patent application WO 02/070673 employs a continuous centrifugation method for isolation of virus from host cells: the cell culture is subjected to continuous centrifugation under conditions effective to concentrate the cells into a pellet, and the pelleted cells are ejected from the centrifuge into a collection receptacle under conditions effective to lyse the cells and thereby obtain a lysate. Lysing the cells according to that method is also within the scope of "lysing the host cells" according to the invention. Such a method should also benefit from the invention, i.e., addition of nuclease to the cell culture before subjecting it to the continuous centrifugation method, the thus improved method resulting in lower nucleic acid contamination in the lysate and, hence, in the final purified product.

Clarification

In preferred embodiments of the invention, the host cell lysate comprising the virus is clarified. Clarification may be done by a filtration step, removing cell debris and other impurities. Suitable filters may utilize cellulose filters, regenerated cellulose fibers, cellulose fibers combined with inorganic filter aids (e.g., diatomaceous earth, perlite, fumed silica), cellulose filters combined with inorganic filter aids and organic resins, or any combination thereof, and polymeric filters (examples include, but are not limited to, nylon, polypropylene, polyethersulfone) to achieve effective removal and acceptable recoveries. In general, a multiple stage process is preferable but not required. An exemplary two- or three-stage process would consist of a course filter(s) to remove large precipitate and cell debris followed by polishing second stage filter(s) with nominal pore sizes greater than 0.2 micron but less than 1 micron. The optimal combination may be a function of the precipitate size distribution as well as other variables. In addition, single stage operations employing a relatively tight filter or centrifugation may also be used for clarification. More generally, any clarification approach including dead-end filtration, microfiltration, centrifugation, or body feed of filter aids (e.g., diatomaceous earth) in combination with dead-end or depth filtration, which provides a filtrate of suitable clarity to not foul the membrane and/or resins in the subsequent steps, will be acceptable to use in the clarification step of the invention.

In certain embodiments, depth filtration and membrane filtration is used. Commercially available products useful in this regard are, for instance, mentioned in WO 03/097797, p. 20-21. Membranes that can be used may be composed of different materials, may differ in pore size, and may be used in combinations. They can be commercially obtained from several vendors.

It has now been found by the present inventors that certain membranes unexpectedly give superior results in the process of the invention, providing much improved clarification compared to other membranes (see, example 4).

It is, therefore, an embodiment of the invention to use a combination of 0.8 µm and 0.45 µm filters, preferably SARTOPORE® 2 filters, for clarification.

Ultrafiltration/Diafiltration

In certain embodiments of the invention, the virus suspension is subjected to ultrafiltration/diafiltration at least once during the process, e.g., for concentrating the virus and/or buffer exchange, and/or for concentration and diafiltration of the clarified harvest. The process used to concentrate the virus according to the method of the invention can include any filtration process (e.g., ultrafiltration (UF)) where the concentration of virus is increased by forcing diluent to be passed through a filter in such a manner that the diluent is removed from the virus preparation whereas the virus is unable to pass through the filter and thereby remains, in concentrated form, in the virus preparation. UF is described in detail in, e.g., *Microfiltration and Ultrafiltration: Principles and Applications*, L. Zeman and A. Zydney (Marcel Dekker, Inc., New York, N.Y., 1996). A preferred filtration process is Tangential Flow Filtration ("TFF") as described in, e.g., MILLIPORE catalogue entitled "*Pharmaceutical Process Filtration Catalogue*," pp. 177-202 (Bedford, Mass., 1995/96). TFF is widely used in the bioprocessing industry for cell harvesting, clarification, and concentration of products including viruses. The system is composed of three distinct process streams: the feed solution, the permeate and the retentate. Depending on application, filters with different pore sizes may be used. In one embodiment of the invention, the retentate is the product and can be used for further purification steps if desired. For this embodiment, the particular ultrafiltration membrane selected will have a pore size sufficiently small to retain virus but large enough to effectively clear impurities.

Depending on the manufacturer and membrane type, for adenovirus, nominal molecular weight cutoffs (NMWC) between 100 and 1000 kDa may be appropriate, for instance, membranes with 300 kDa or 500 kDa NMWC. The membrane composition may be, but is not limited to, regenerated cellulose, polyethersulfone, polysulfone, or derivatives thereof. The membranes can be flat sheets or hollow fibers. UF is generally referred to filtration using filters with a pore size of smaller than 0.1 µm. Products are generally retained, while volume is reduced through permeation. The two most widely used geometries for TFF in the biopharmaceutical industry are plate and frame and hollow fiber modules. Hollow fiber units for ultrafiltration and microfiltration were developed by Amicon and Ramicon in the early 1970s (M. Cheryan, *Ultrafiltration Handbook*), even though now there are multiple vendors including Spectrum and A/G Technology. The hollow fiber modules consist of an array of self-supporting fibers with a dense skin layer that give the membranes its permselectivity. Fiber diameters range from 0.5 mm-3 mm. An advantage of hollow fiber modules is the availability of filters from small membrane areas (ca. 16 cm$^2$) to very large membrane areas (ca. 28 m$^2$) allowing linear and simple scale-up. In certain preferred embodiments according to the invention, hollow fibers are used for TFF. These are reported to give less shear and a better viral particle/infectious unit (VP/IU) ratio than flat screen membranes. In certain embodiments, hollow fibers of 0.05 µm are used according to the invention.

Diafiltration (DF), or buffer exchange, using ultrafilters is an ideal way for removal and exchange of salts, sugars, non-aqueous solvents separation of free from bound species, removal of material of low molecular weight, or rapid change of ionic and/or pH environments. Microsolutes are removed most efficiently by adding solvent to the solution being ultrafiltered at a rate equal to the UF rate. This washes microspecies from the solution at a constant volume, purifying the retained virus. The invention utilizes a DF step to exchange the buffer of the lysate prior to further chromatography or other purification steps. According to one embodiment of the invention, DF by TFF is performed for buffer exchange, wherein the addition of buffer equals the removal of permeate.

UF/DF can be used to concentrate and/or buffer exchange the virus suspensions according to the invention, in different stadia of the purification process, e.g., the lysate and/or further purified virus suspensions such as those that have undergone chromatography.

In one embodiment according to the invention, the lysate is concentrated by UF/DF five-fold, and the resulting concentrated virus suspension is buffer exchanged with six diafiltration volumes (DFV) of a buffer comprising 1 M NaCl, using a constant volume diafiltration method. It was found that this high salt concentration significantly improves the quality of the resulting virus, as many undesired proteins were lost during this step (see, example y2). It is, therefore, an embodiment according to the invention that the clarified lysate is exchanged against a solution comprising 0.8-2.0 M NaCl, e.g., around 1 M NaCl, or another salt providing an equivalent ionic strength. Both the anion and the cation of the salt can be changed.

Before the virus suspension is subjected to anion exchange chromatography, it may be buffer exchanged with a buffer comprising 0.4 M NaCl, or another salt providing an equivalent ionic strength. In certain embodiments, this is accomplished by constant volume diafiltration, using four DFVs of the desired buffer.

Further Purification

According to preferred embodiments of the invention, the virus suspension that has been obtained by the method according to the invention, preferably after clarification of the lysate, is further purified, e.g., by methods generally known to the person skilled in the art. This may, for instance, be achieved by density gradient centrifugation as, for instance, discussed in WO 98/22588, p. 59-61.

Preferably however, further purification employs at least one chromatography step as, for instance, discussed in WO 98/22588, p. 61-70. Many processes have been described for the further purification of viruses, wherein chromatography steps are included in the process. The person skilled in the art will be aware of these processes, and can vary the exact way of employing chromatographic steps to optimize the process of the invention.

It is, for instance, possible to purify certain viruses by a combination of anion exchange and cation exchange chromatography steps, see U.S. Pat. No. 6,008,036.

It is also possible to employ a hydroxyapatite medium for purifying adenovirus, see WO 02/44348.

A reversed-phase adsorption step might also be used as, for instance, described in WO 03/097797, p. 26.

For adenovirus purification, it is preferred to use at least one anion exchange chromatography step. After the anion exchange chromatography step, the virus may be sufficiently pure. In certain embodiments, however, a size exclusion chromatography step is further performed to increase the robustness of the process. This step may be prior to or after the anion exchange chromatography step. Other purification steps may also be suitably combined with an anion exchange chromatography step.

The use of anion exchange chromatography for adenovirus purification has been extensively described and this aspect is, therefore, well within the reach of the person skilled in the art. Many different chromatography matrices have been employed for purification of adenovirus and are suitable, and the person skilled in the art can easily find the optimal anion exchange material for purifying the virus, for instance, guided by the following art.

U.S. Pat. No. 5,837,520 (see, also Huyghe et al., 1995, *Human Gene Therapy* 6: 1403-1416) describes a method of purifying adenovirus wherein the host cell lysate is treated with a nuclease, followed by anion exchange and metal ion affinity chromatography.

U.S. Pat. No. 6,485,958 describes the use of strong anion exchange chromatography for purification of recombinant adenovirus.

Anion exchange chromatography has been employed with fluidized bed columns for the purification of adenovirus particles, see WO 00/50573.

Further, expanded bed anion exchange chromatography and certain chromatographic resins for anion exchange chromatography for purification of adenovirus particles have been described in U.S. Pat. No. 6,586,226.

In addition to anion exchange columns, anion exchange membrane chromatography products such as those produced by Pall (e.g., Mustang™ series) and Sartorius (e.g., Sartobind series) are suitable. For use of these filters and their advantages in adenovirus purification see, for instance, WO 03/078592. Employment of such filters also falls within the scope of the term "anion exchange chromatography" as used herein.

U.S. Pat. No. 6,537,793 describes the purification of adenoviral particles from host cells using ion-exchange chromatography, in particular, teaching a preference for Q Sepharose XL types of chromatographic support for this purpose. In one embodiment of the invention, an adenovirus is further purified using a Q Sepharose XL column.

As described above, the process may further suitably employ a size exclusion chromatography step.

International application WO 97/08298 describes the purification of adenoviruses using certain chromatographic matrices to prevent damage to the viruses, including anion exchange and size exclusion steps.

U.S. Pat. No. 6,261,823 describes a method for purifying adenovirus wherein the adenovirus preparation is subjected to anion exchange chromatography followed by size exclusion chromatography. In the size exclusion step, a group separation of viral particles from impurities of low molecular weight is achieved. According to certain embodiments of the invention, about 15-30%, preferably about 20%, of the column volume is loaded on the size exclusion column (group separation mode of size exclusion chromatography).

Hence, in an embodiment of the invention, an adenovirus suspension that has been prepared according to the method of the invention is further purified using an anion exchange chromatography step and a size exclusion chromatography step.

WO 03/078592 describes the use of high-throughput anion exchange filters (i.e., a charged filter that contains anion exchange groups) for adenovirus (Ad5) purification. The following advantages are described for such charged filters compared to anion exchange columns: (i) faster flow rates, (ii) higher binding capacity, (iii) higher virus recovery, (iv) no packing or cleaning validation required for clinical use, and (v) no lifetime issues or storage issues when disposable filter cartridges are used. As described above, the use of such anion exchange filters is an embodiment of the invention, and is an embodiment considered included within the scope of "anion exchange chromatography" in the invention. However, in addition to being an equivalent for column chromatography, the present inventors have surprisingly found an advantage for purifying adenovirus serotype 35 (Ad35) using an anion exchange filter, over the use of an anion exchange column: certain adenovirus proteins that were not incorporated into adenovirus particles are separated from the adenovirus particles by use of an anion exchange filter, not by an anion exchange column. Such free adenovirus proteins were not previously found in preparations of recombinant adenovirus particles and would normally go undetected, but now can be removed using the step of subjecting a recombinant adenovirus preparation comprising free adenovirus proteins to a charged filter that contains anion exchange groups. This effect of the use of the charged filter was not noted in WO 03/078592. In addition, WO 03/078592 does not disclose the employment of anion exchange filters for the purification of Ad35, or other adenovirus particles of subgroup B. The invention, therefore, provides a method for removing free adenovirus proteins from a recombinant adenovirus preparation, comprising the step of: subjecting a recombinant adenovirus preparation comprising free adenovirus proteins to a charged filter that contains anion exchange groups. Without wishing to be bound by theory, it is conceivable that the possibly somewhat lower stability of recombinant adenovirus particles of subgroup B (see, e.g., WO 2004/001032) gives rise to the hitherto undetected free adenovirus proteins that appear not incorporated into adenovirus particles. Hence, this particular method according to the invention may be particularly beneficial for purification of recombinant adenovirus of subgroup B, such as Ad35, Ad11, etc. However, it is also possible that the method improves purification of the more stable Ad5- or Ad2-based adenovirus. Provided is the use of an anion exchange filter for the removal of free (i.e., not incorporated into viral particles) adenovirus proteins from a recombinant adenovirus preparation. Preferably, the recombinant adenovirus preparation comprises recombinant subgroup B adenovirus, such as recombinant Ad35. The invention also provides a method for purification of recombinant subgroup B adenovirus particles, such as Ad35 particles, the method comprising a step of subjecting the recombinant subgroup B particles, such as Ad35, to an anion exchange filter purification step. Anion exchange filters suitable for use in these methods of the invention are known in the art and commercially available (see, WO 03/078592, paragraphs [40]-[41]), e.g., from Pall (e.g., Mustang™ series) and from Sartorius (e.g., Sartobind series).

Buffers

Many buffers can be used during purification of the virus according to the invention. In several embodiments of the invention, buffers used for UF/DF and anion exchange chromatography in general contained 0.4-1.0 M NaCl/50 mM TRIS pH 7.5, wherein the concentrations of NaCl were dependent on the process step. In certain embodiments, the buffers used after clarification are free of detergent, magnesium chloride and sucrose. The absence of these additives distinguishes these buffers from those used in known established protocols. Nevertheless, when the methods according to the invention are employed, a purified and substantially non-aggregated adenovirus is obtained. An advantage of the use of buffers without these additives is that they are easier to prepare, cheaper, and that there is no need to test for removal of the additives.

In one embodiment according to the invention, the adenovirus is buffer exchanged during group separation to, and finally stored in, the buffer that is also used for the Adenovirus World Standard (Hoganson et al., "Development of a stable adenoviral vector formulation," *Bioprocessing* March 2002, p. 43-48): 20 mM Tris pH 8, 25 mM NaCl, 2.5% glycerol.

Many other buffers can be used and several examples of suitable formulations for the storage and pharmaceutical administration of purified (adeno)virus preparations can, for instance, be found in European Patent No. 0853660, and in international patent applications WO 99/41416, WO 99/12568, WO 00/29024, WO 01/66137, WO 03/049763, the contents of the entirety of each of which are incorporated herein by this reference.

Vectors with Specific Inserts

In the art, the transgene itself is generally regarded as irrelevant for the purification process. However, as shown herein, the transgene may, in specific cases by its expression in the host cell or in the virus, influence properties of the virus or may have an influence on the process of purifying the virus.

One such, non-limiting, specific case as found by the present inventors, is where the transgene is the Ebola virus nucleoprotein. Purifying an adenoviral vector containing the Ebola virus nucleoprotein gene with the standard purification procedure results in co-purifying the expressed Ebola virus nucleoprotein. No co-purification of several other transgene-expressed proteins was observed (for instance, not with Ebola glycoprotein dTM (Sudan), Ebola Glycoprotein dTM (Zaire), or measles hemagglutinin protein (MV-H)). This suggests a specific interaction between the Ebola nucleoprotein and Adenovirus, which seems to depend on the characteristics of the Ebola nucleoprotein. Other nucleic acid binding proteins are expected to have similar characteristics and are expected to have an interaction with Adenovirus resulting in co-purification as well. For adenoviruses having such transgenes, including nucleic acid binding proteins, such as nucleoproteins, i.e., Ebola virus nucleoprotein, it is beneficial to exchange the buffer to salt concentrations that are even higher than 1 M NaCl, and use, for instance, 2-5 M NaCl buffers to improve the final product quality (see, example 3). Buffer exchange may suitably be performed by TFF.

Alternatively, other methods for buffer exchange could be used, for instance, the salt could be added to the virus suspension directly in a gradual way by addition of the solid material or concentration solution. This aspect of the invention may be beneficially combined with other aspects of the invention, for instance, with adding the nuclease before lysis, but is not limited thereto. It is described herein that use of such high salt buffers unexpectedly does not result in aggregation problems, or in significant deterioration of the infectivity or integrity of the purified viral particles. In this aspect, the buffer exchange step preferably takes place after the elution of the virus from anion exchange chromatography, and preferably before a further purification step. Such a further purification step may, for instance, be a size exclusion step in group separation mode.

Figure 9:
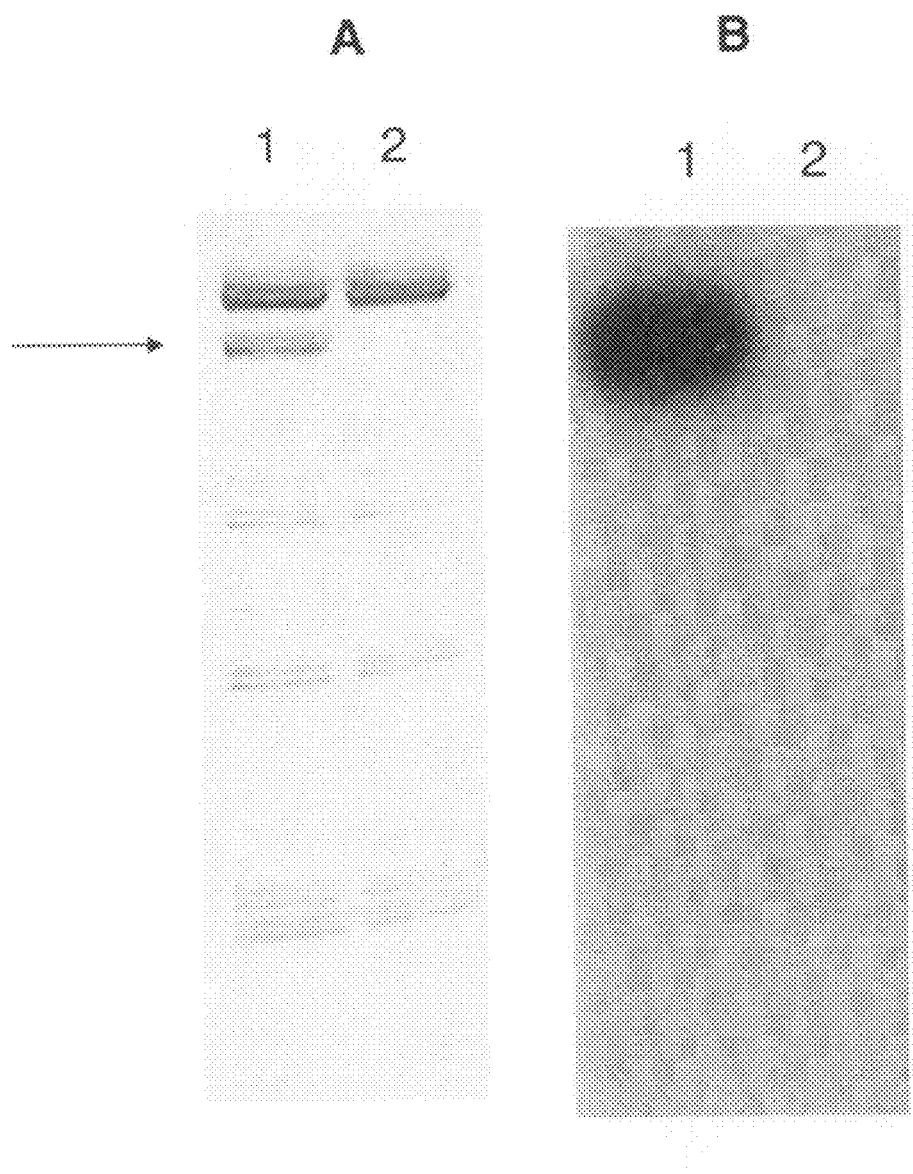
Figure 10:
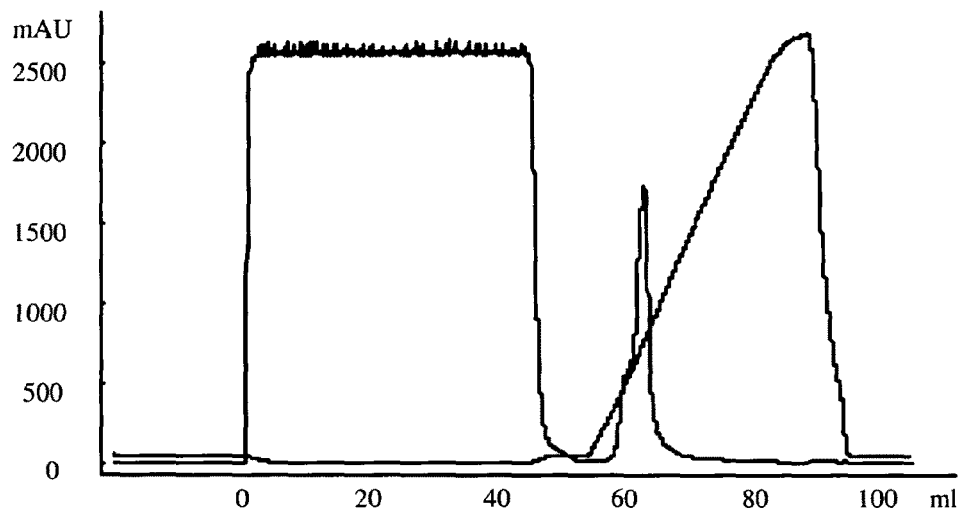
Figure 10:
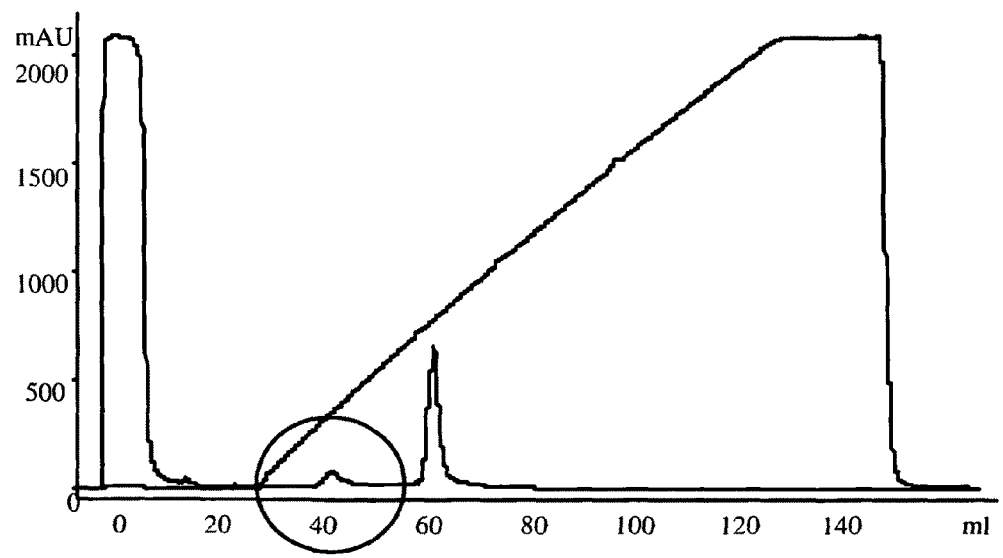

This last step can be used for polishing the virus suspension, i.e., removing minor impurities that may still be present after anion exchange, but also for buffer exchange directly on the group separation column. Alternatively, instead of size exclusion, the further purification step may comprise a filtration of the virus suspension comprising the high salt concentration through a hydrophilic filter, such as a Durapore PVDF filter (e.g., Millipac from Millipore) or a SARTOPORE® 2 filter. The filter preferably has a pore size of 1.2 μm, more preferably smaller, e.g., 1.0 μm, still more preferably smaller, e.g., 0.8 μm, 0.45 μm or 0.22 μm. Unexpectedly, the nucleoprotein (NP) of Ebola virus was found to be separated from a recombinant adenovirus under these conditions by being retained by the filter, while NP, having a molecular weight of about 100 kD, was expected to pass through the filter pores together with the adenovirus. Use of these filters provides a fast solution for separating the nucleoprotein from the virus, as no prolonged incubation in high salt is required for this procedure, while it allowed complete removal of the nucleoprotein from the virus (FIG. 9). Size exclusion chromatography step may still be employed after such a filtration step, to remove other minor contaminants and/or for buffer exchange.

Use of high salt for removing DNA binding proteins is an aspect of the invention that is expected to be useful for viruses other than adenoviruses. In that case, another column chromatography step may be applied instead of anion exchange chromatography. The important factor seems to be the removal of sufficient contaminating material before the high salt step is applied. This removal could be achieved by means other than anion exchange chromatography, also for recombinant adenoviruses.

Hence, the invention further provides a method for the production of a virus comprising a nucleic acid sequence coding for a nucleic acid binding protein, comprising the steps of: a) culturing host cells that have been infected with virus, b) subjecting the culture of host cells and the virus therein produced to lysis of the host cells to provide a lysate comprising the virus, c) subjecting the virus to anion exchange chromatography, characterized in that after anion exchange chromatography the virus-containing mixture is buffer exchanged with a solution comprising at least 1 M NaCl, or another salt providing an equivalent ionic strength. Preferably, the virus is further purified using at least one step comprising either filtration though a hydrophilic filter and/or using at least one step comprising size exclusion chromatography. For these embodiments, a solution comprising at least 1 M NaCl or another salt providing equivalent ionic strength is referred to as a "high salt" solution.

Both the anion and the cation can be varied as is known to the person skilled in the art, as long as sufficient ionic strength is provided without precipitation or other undesired side-effects such as inactivation of the virus, as the method likely depends on the breaking of ionic interactions between the DNA binding protein and the purified virus. For example, NaCl may be in part or wholly substituted for other salts, such as, KCl, sodium phosphate, CsCl, LiCl, $(NH_4)_2SO_4$, $NH_4Cl$, NaBr, NaI, KBr, KI, $KNO_3$, $NaHCO_3$, $KHSO_4$, etc. A 5× dilution of the buffer used in the example of the invention (comprising 5 M NaCl) had a conductivity of 78-79 mS/cm.

Buffers containing other salts and having a similar or higher conductivity can, for instance, now easily be tested for suitability in removing DNA binding proteins from partially purified virus, according to the invention. It is expected that this embodiment will work up to saturation of the NaCl concentration (this is about 6 M NaCl), but for practical reasons, it is preferred to use buffers that are not saturated, e.g., 5 M NaCl. Preferably, the solution comprises at least 1.5 M NaCl or another salt providing an equivalent ionic strength. More preferably, the solution comprises at least 2 M NaCl or another salt providing an equivalent ionic strength. Even more preferably, the solution comprises at least 3 M NaCl or another salt providing an equivalent ionic strength. Even yet more preferably, the solution comprises at least 4 M NaCl or another salt providing an equivalent ionic strength. Most preferably, the solution comprises around 5 M Na Cl or another salt providing an equivalent ionic strength. The high salt solution comprising the virus may be incubated for a certain time, preferably at least one hour, more preferably at least two hours. In general, the examples show an increased purification of the DNA binding protein from the virus when incubation is longer, at least up to overnight. Further, a higher ionic strength appears to improve the purification.

Hence, it is conceivable that even at ionic strengths of 1 M or 1.5 M NaCl and prolonged incubation, e.g., for at least two days or one week, there may be purification of the DNA binding protein from the virus. This can be routinely checked by the experiments described herein. Overnight incubation of recombinant adenovirus expressing Ebola virus nucleoprotein in a buffer comprising 5 M NaCl, removed the contaminating nucleoprotein from the virus to below detection limits and is, therefore, an embodiment of the invention. In certain embodiments, the virus is a recombinant adenovirus. In certain embodiments, the nucleic acid binding protein is a nucleoprotein of a virus. In certain embodiments thereof, the nucleic acid binding protein is the Ebola virus nucleoprotein. In certain embodiments, the buffer exchange step takes place after anion exchange chromatography and before a filtration and/or size exclusion chromatography step. It is further preferred to include a nuclease treatment of the lysate, whereby preferably the nuclease is added to the cell culture before lysis is complete, in accordance with other aspects of the invention. Instead of high salt or in addition thereto, detergent may be added to purify the virus from contaminating DNA binding protein. In one experiment, the inventors have shown that addition of 1% TWEEN 20® also significantly reduced the contaminating nucleoprotein from recombinant adenovirus expressing Ebola nucleoprotein. Other detergents can suitably be tested and the concentration may be varied, e.g., between about 0.2% and 5%, to find optimal conditions for removal of DNA binding proteins from recombinant virus preparations according to the invention. In this aspect, preferably at least 1% detergent is added. The first experiments of the inventors, however, have indicated a higher reproducibility of high salt incubation for this purpose and, therefore, this is preferred.

Batches of Recombinant Adenovirus

In one aspect, provided is a batch of recombinant adenovirus comprising a transgene chosen from the group consisting of: an Ebola virus nucleoprotein, an Ebola virus glycoprotein, a *Plasmodium falciparum circumsporozoite* gene, and a measles virus hemagglutinin, the batch characterized in that it contains less than 0.1 ng host cell DNA per 1E11 viral particles. These transgenes may optionally contain deletions, additions, and/or mutations compared to the wild-type sequences found in nature, including all isolates or subtypes, without deviating from the scope of this aspect of the invention. In preferred aspects, the batch is characterized in that it contains less than 0.08 ng, more preferably less than 0.06 ng, still more preferably less than 0.04 ng host cell DNA per $10^{11}$ viral particles.

EXAMPLES

The following examples are included to further illustrate the invention by means of certain embodiments of the invention, and are not to be construed to limit the scope of the invention in any way.

Example 1

Addition of Nuclease to the Cell Culture Instead of to the Host Cell Lysate Improves the Process for Virus Purification In this example, it is shown that addition of nuclease to the cell culture before lysing the cells reduces the amount of residual host cell DNA in the final purified bulk.

In runs 1 and 2, a 10 liter PER.C6® cell culture was lysed with 1% TRITON® X-100 (Sigma) at day 2.5 after infection with an adenoviral vector. Thirty minutes after lysis, BENZONASE® (Merck KgaA, 50 units/ml) and $MgCl_2$ (2 mM) were added. After another 30 minutes, the TRITON® X-100/ BENZONASE® (T/B) harvest was clarified by filtration. This, therefore, was a run according to processes known in the art.

In runs 3-8, BENZONASE® (50 U/ml) and $MgCl_2$ (2 mM) were added to 10 liter PER.C6® cell culture (day 2.5 post infection), and after ten minutes incubation, the cells were lysed with 1% TRITON® X-100. After an additional incubation of 50 minutes, the BENZONASE®/TRITON® X-100 (B/T) harvest was clarified by filtration.

The difference with the processes known from the art, therefore, is in the order in which the nuclease (BENZONASE®) and the detergent (TRITON® X-100) were added: classically, first the cells are lysed and subsequently, nuclease is added (referred to herein as T/B harvest), whereas in the process according to the invention, first, nuclease is added and subsequently, the cells are lysed (referred to herein as B/T harvest). This is schematically shown in FIG. 1.

The samples were then further purified. Clarification was performed by depth filtration (0.5 µm Clarigard filter, Millipore) followed by further clarification over a 0.8/0.45 µm SARTOPORE® 2 (Sartorius) filter. The clarified material was concentrated five times over a 0.05 µm hollow fiber (Spectrum), followed by diafiltration with subsequently six volumes of 1.0 M NaCl/50 mM TRIS pH 7.5 and four volumes of 0.4 M NaCl/50 mM Tris pH 7.5. The diafiltered retentate was loaded onto a Sepharose Q-XL (Amersham) column and the virus fraction was eluted with 0.55 M NaCl/ 50 mM TRIS pH 7.5. This fraction was further purified and buffer exchanged with a Sepharose 4 FF (Amersham) column. The generated purified bulk was concentrated to the desired concentration with a hollow fiber (0.05 µm poresize, Spectrum), 0.22 µm filtered and aliquotted. Purified bulk samples were analyzed for residual host cell DNA by Q-PCR.

The T/B treatment resulted in a reduction of DNA that, after further downstream processing, could just meet the required specification in the filled and finished material. Regulatory requirements for residual host cell DNA for life virus formulations are <10 ng per dose (assumed that a dose contains 1E11 viral particles).

As is shown in Table 1, reversing the TRITON® X-100 and BENZONASE® steps reduced the amount of residual host cell DNA in the purified bulk significantly: by the addition of nuclease before active cell lysis, the amount of residual host cell DNA could be reduced 10 to 40 times, to less than 0.1 ng/1E11 viral particles.

SDS-PAGE analysis (FIG. 2) indicates that upon clarification by depth and membrane filtration of a B/T harvest, a number of host cell proteins, among which a significant amount of histon proteins ($M_w$ around 10-20 kD on gels, identity confirmed by mass spectrometry), was removed during clarification, while these proteins are still present in the clarified T/B harvest.

Hence, the process according to the invention results in significant advantages over those known from the prior art. Without wishing to be bound by theory, possible explanations for the differences between runs 1 and 2 (T/B) on one side and runs 3-8 (B/T) on the other side may include:

1. Upon addition of BENZONASE®, the DNA released from cells lysed due to virus production can already be digested. As soon as DNA is released from cells lysed by TRITON®, the BENZONASE® is present to immediately digest the DNA, thereby preventing the formation of large DNA aggregates. Digestion of non-aggregated DNA is probably more effective than digestion of major DNA aggregates.

2. The total incubation time of BENZONASE® increases with 30 minutes, resulting in more effective digestion (see, BENZONASE® brochure Merck KGaA code W 214950).

3. Possibly, larger histon complexes are formed when the DNA is digested immediately upon release and these larger particles are retained by the clarification filters. Retainment of histon-DNA complexes during clarification might also have contributed to reduction of residual host cell DNA.

Several anion exchange resins have been tested, e.g., QAE 550C and Super Q 650M (purchased from Tosoh), Q Sepharose HP, ANX Sepharose 4FF, DEAE Sepharose, Q Sepharose XL, Q Sepharose Big Bead and Q Sepharose FF (purchased from Amersham). Although all these resins were suitable for the purification of the recombinant adenoviruses, Q Sepharose XL appeared best suitable based on separation of virus from host cell proteins and host cell DNA and flow characteristics.

Several size exclusion resins were tested, e.g., Sephacryl S300, Sephacryl S500 Sepharose 4FF and Sepharose 6 FF (all purchased from Amersham). Although all these resins were suitable for the purification of the recombinant adenoviruses, Sepharose 4 FF appeared best suitable based on ability to separate virus from host cell proteins and DNA.

Based upon these and other results (see, below), a preferred process according to the invention is shown schematically in FIG. 4.

Example 2

Buffer Exchange with High Salt Buffer Improves Virus Process

Figure 3:
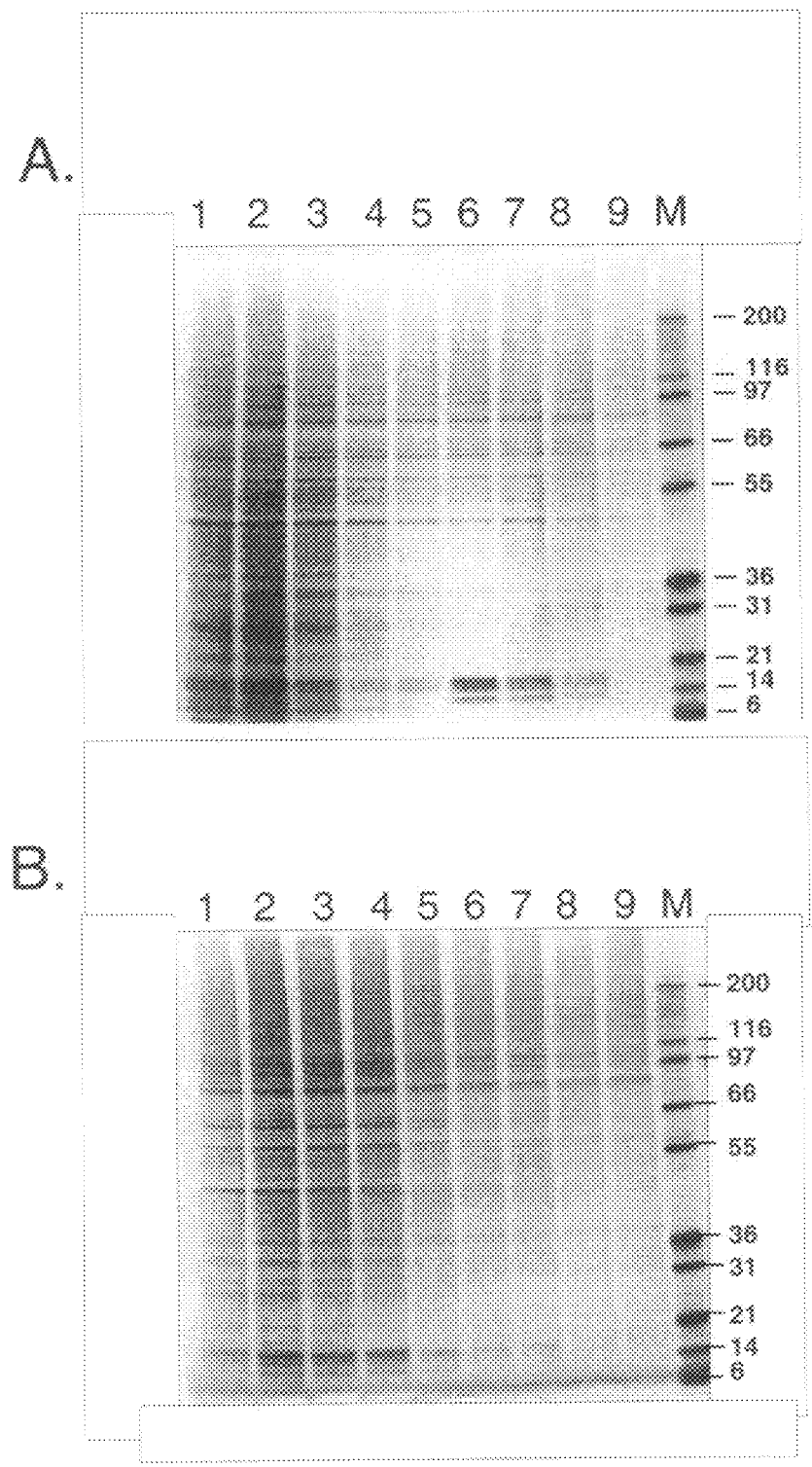

PER.C6® cells were grown in a 10 L bioreactor and infected with Ad5.Adapt.MV-H (with measles virus hemagglutinin as transgene, described in WO 2004/037294). Two and a half days after infection, the cells were lysed with 1% TRITON® X-100 and after 30 minutes, BENZONASE® (50 units/ml) and $MgCl_2$ were added and incubated for another 30 minutes. The harvest was clarified over a 0.5 μm Clarigard filter and subsequently by a Millistak DE 30/60 filter (Millipore). The clarified harvest was diluted with an equal volume of 0.6 M NaCl/50 mM HEPES pH 7.5, resulting in a final concentration of 0.3 M NaCl. The diluted clarified harvest was concentrated four times with a 500 kD flatscreen cassette (Biomax 500, Pellicon 2 module Millipore) and subsequently diafiltered with two diafiltration volumes (DFV) of 0.3 M NaCl/50 mM HEPES pH 7.5; two DFV of 0.6 M NaCl/50 mM HEPES pH 7.5; two DFV of 1.0 M NaCl/50 mM HEPES pH 7.5; and three DFV of 0.3 M NaCl/50 mM HEPES pH 7.5. The conductivity of the generated permeates was measured and the samples were analyzed by SDS-PAGE (FIG. 3). The data showed that histones ($M_w$ around 10-20 kD on gels, identity confirmed by mass spectrometry) are passing the membrane pores when the salt concentration of the permeate (and, therefore, of the retentate) is in the range of 0.55 and 0.85 M NaCl, or higher.

A possible explanation is that an electrostatic interaction is broken under these salt conditions resulting in release of histones from complexes allowing passage through 500 kD pores.

From this experiment, it is concluded that introduction of a high salt buffer during the UF/DF step results in more efficient removal of host cell proteins, especially histon proteins.

Figure 2:
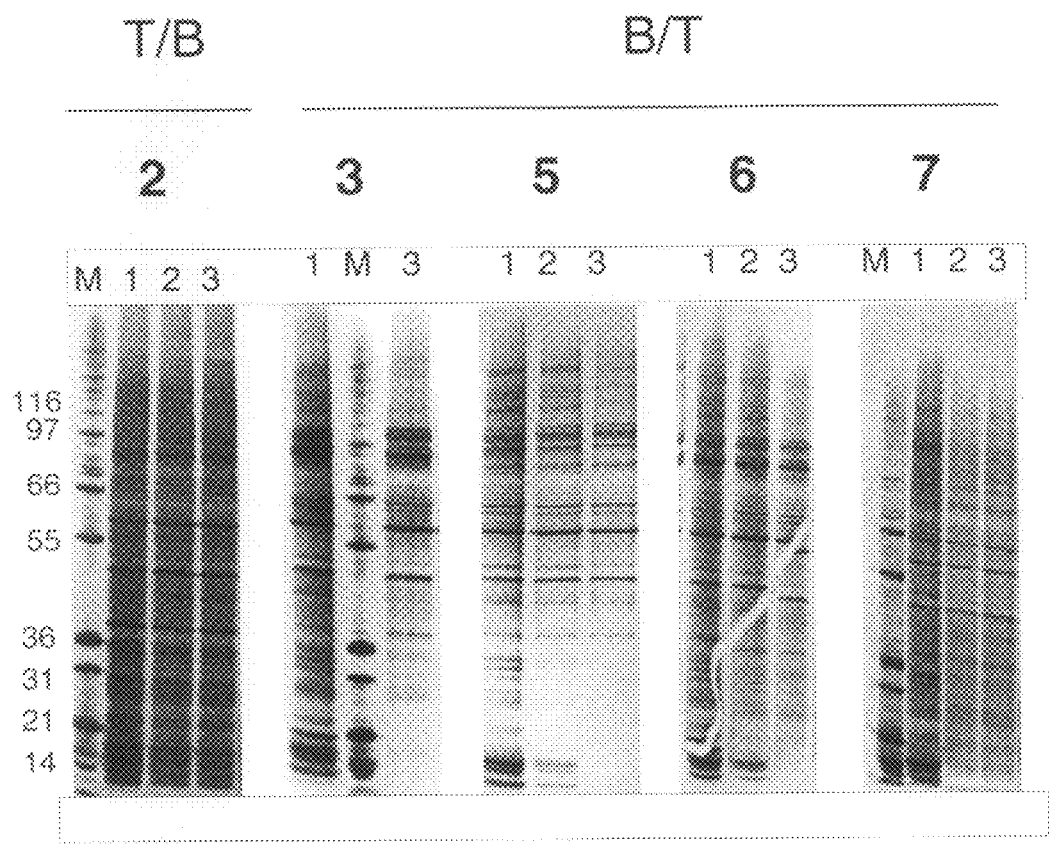

Although in this example the cells were lysed first and subsequently treated with nuclease (T/B), the diafiltration against buffer with high salt strength (higher than 0.55 M NaCl, for instance, 1 M NaCl) is likely also beneficial in the process according to the invention, wherein the nuclease is added to the cells before they are lysed (B/T, see example 1), even though in the B/T process, there is already less histon contamination (see, FIG. 2).

Figure 4:
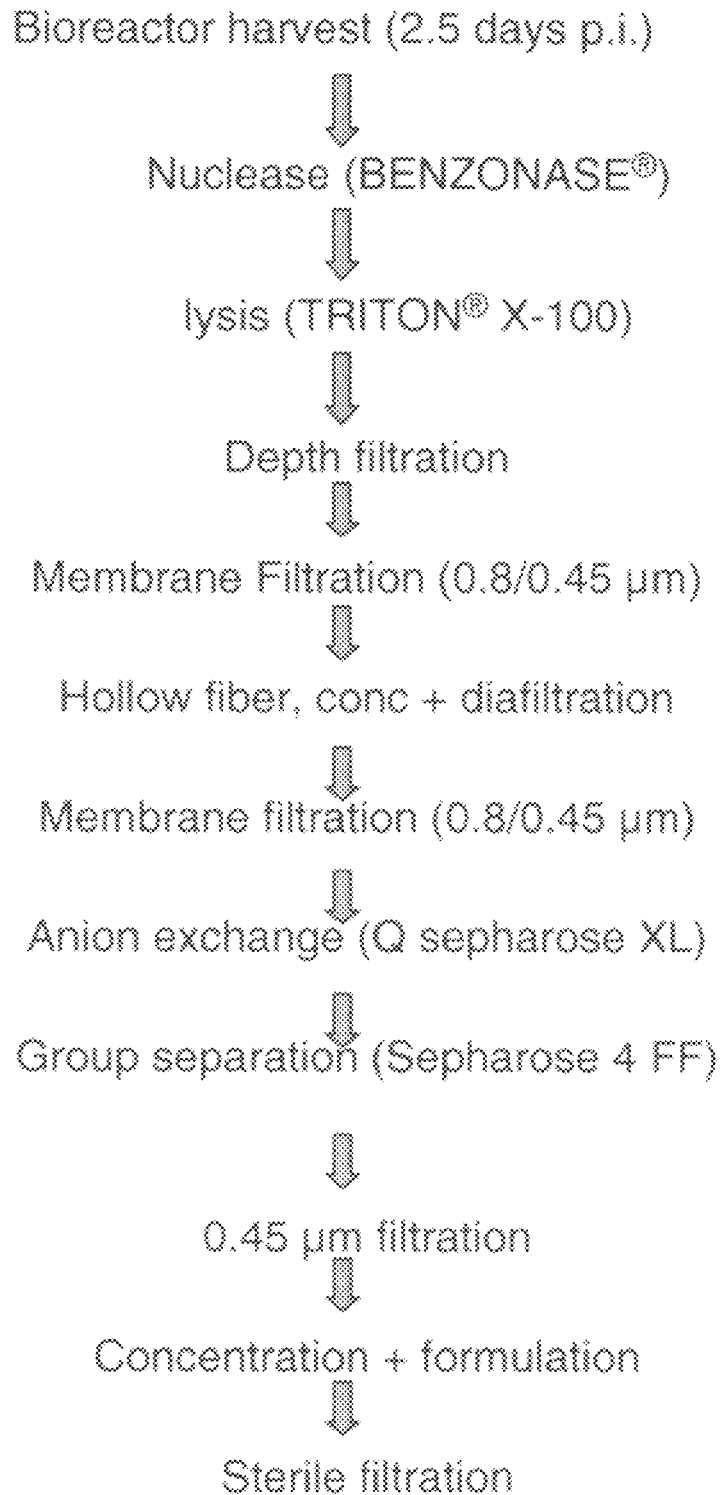

Therefore, in an embodiment of the process according to the invention, the clarified lysate is exchanged against a solution comprising 0.8-2.0 M NaCl, preferably about 1 M NaCl, or another salt providing an equivalent ionic strength (see, example 1 and FIG. 4).

Example 3

Removal of Contaminating Nucleoprotein from Recombinant Virus Preparations

Generation of recombinant adenovirus with Ebola nucleoprotein as a transgene is described in example 5. In this example, the purification of such virus is described.

Experiment 3.1

Figure 5:
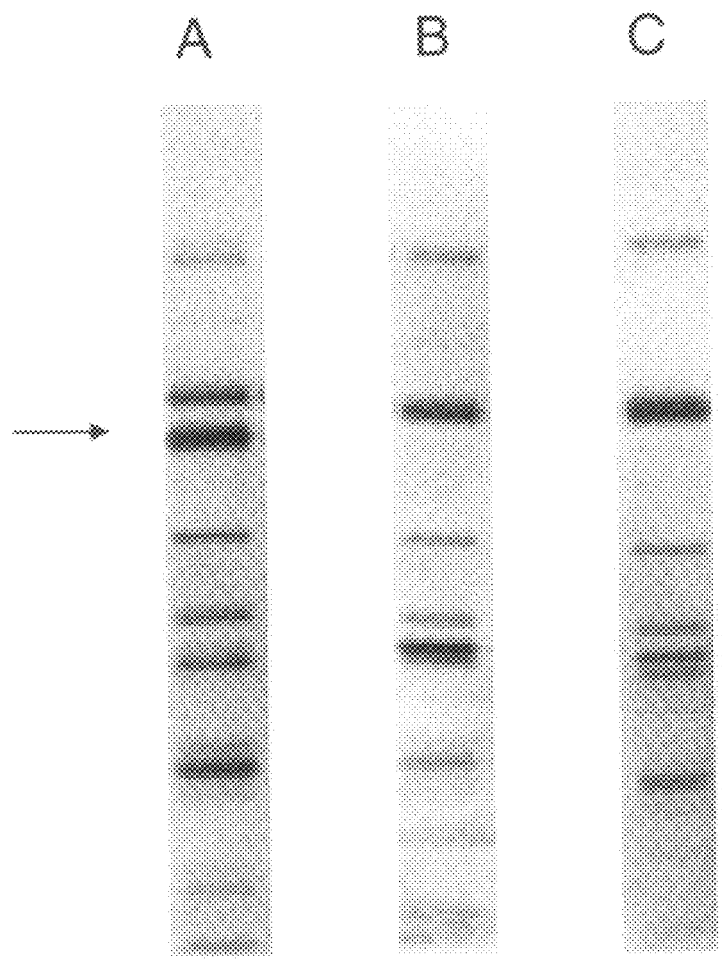

Ad5dE3x.Adapt.Ebo.NP was purified with the described protocol (see, example 1, FIG. 4). This method resulted in co-purification of the expressed Ebola nucleoprotein (NP) transgene with the virus. Filled and finished product was diluted 1:2 with a buffer containing either 5 M NaCl (final concentration 2.5 M) or 2% TWEEN 20® (final concentration 1%) and incubated for one hour at room temperature before loading onto a Sepharose 4 FF column. The void and retarded fractions were analyzed by SDS-Page. The results (FIG. 5) show that the void fraction contained Adenovirus type 5 without contaminating intact NP. Thus far, the results with the high salt appeared reproducible, whereas those with the detergent were not, and hence, high salt is preferred. Optimal conditions for detergent, however, can be tested by varying the detergent used and its concentration.

Conclusion: The Ad5dE3x.Adapt.Ebo.NP vector can be purified from the Ebola nucleoprotein by incubation in a buffer containing either 2.5 M NaCl or 1% TWEEN®, preferably 2.5 M NaCl, followed by separation on 4 FF sepharose.

Experiment 3.2

Ad5dE3x.Adapt.Ebo.NP was purified with the described protocol (see, example 1, FIG. 4). Filled and finished product was dialyzed with a 10 kD membrane against a 50 mM TRIS buffer pH 7.5 containing 1, 2, 3 or 5 M NaCl. The Ad5.Ebo.NP was incubated in these buffers for two hours or overnight before loading onto a Sepharose 4 FF column. The void and retarded fractions were analyzed by SDS-PAGE. The results show that the void fraction contained Adenovirus type 5 with significantly less NP. As shown in Table 2, the amount of removal of NP relates to the salt concentration and incubation time.

Conclusion: The Ad5dE3x.Adapt.Ebo.NP vector can be purified from the Ebola nucleoprotein by incubation in a buffer containing either 2-5 M NaCl followed by separation on 4 FF sepharose. A longer incubation time and a higher salt concentration before separation on the 4 FF column results in higher purity of the Ad5.Ebo.NP vector (more removal of nucleoprotein).

Concentrations of 1 M and 1.5 M NaCl are tested with longer incubation times (e.g., two days, one week) according to this same method to find out whether a longer incubation time may suffice for purification at these salt strengths.

Experiment 3.3

Figure 6:
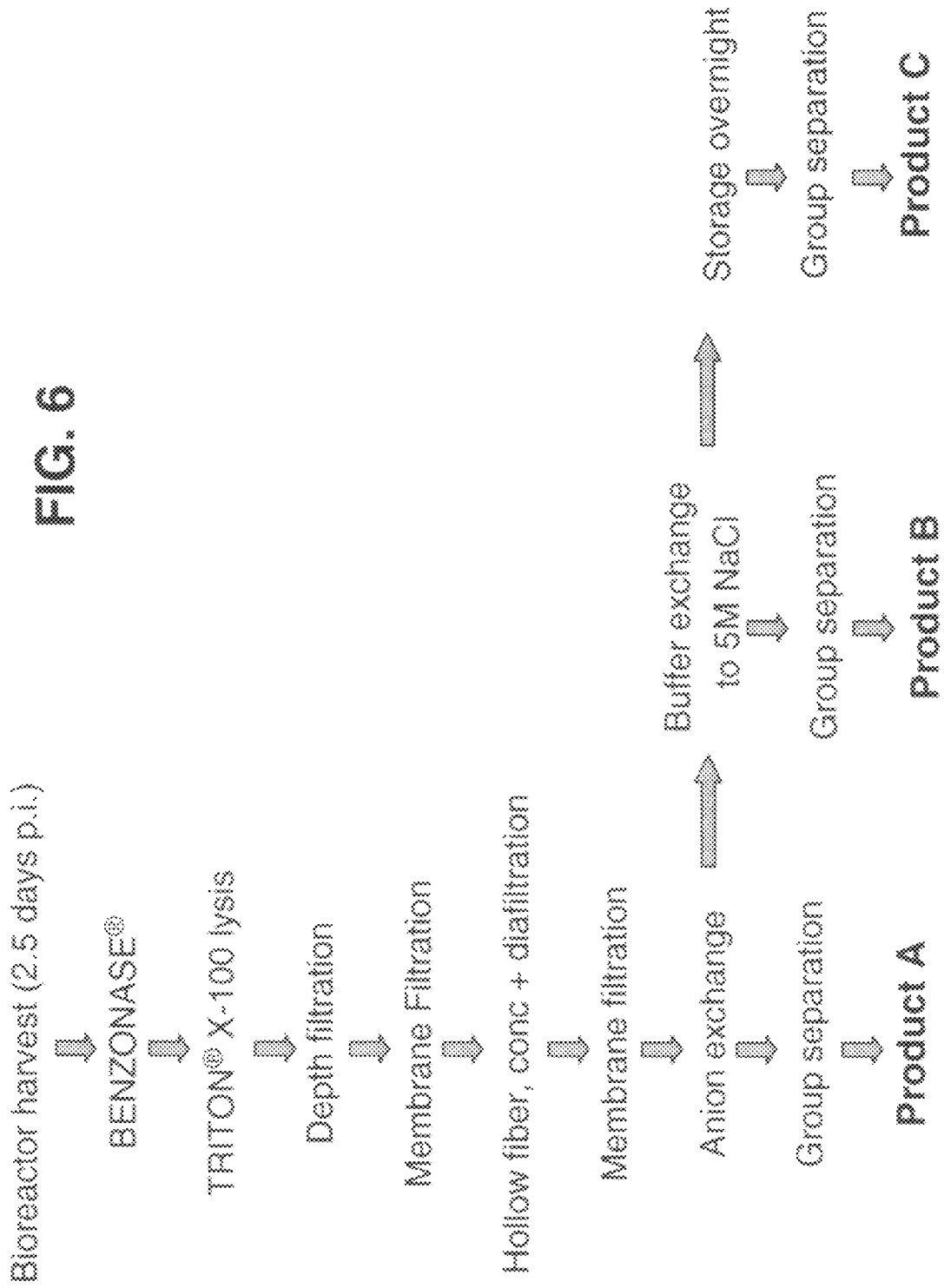

The experiment is schematically indicated in FIG. 6.

PER.C6® cells were grown in a 10 L bioreactor and infected with Ad5.dE3x.Adapt.Ebo.NP. Two and a half days after infection, BENZONASE® (50 units/ml) and $MgCl_2$ were added to the cell culture and after ten minutes, the cells were lysed with 1% TRITON® X-100 and incubated for another 50 minutes. The harvest was clarified over a 0.5 μm Clarigard filter and subsequently by a SARTOPORE® 2 filter (0.8/0.45 μm, Sartorius).

The clarified harvest was split in two portions. One portion was concentrated five times and diafiltered against a buffer containing 5 M NaCl/50 mM Tris pH 7.5 by use of a 0.5 μm hollow fiber (Spectrum). This resulted in an increase of trans membrane pressure (TMP) and a reduction in permeate flux, while the visual appearance of the retentate turned to white and less transparent, indicating precipitation of proteins.

The second portion of clarified harvest was concentrated five times and diafiltrated with six DFV of 1.0 M NaCl/50 mM TRIS pH 7.5 followed by four DFV of 0.4 M NaCl/50 mM TRIS pH 7.5 by use of a 0.5 Mm hollow fiber (Spectrum). The final retentate was purified over a Sepharose Q-XL column (Amersham).

The Q-XL eluate was also divided into two portions. One portion was further purified and buffer exchanged to 25 mM NaCl/20 mM TRIS/2.5% glycerol (formulation buffer) over a size exclusion column (Sepharose 4 FF) in group separation mode (loading of 20% of column volume); this is product A in FIG. 6. The other portion was diafiltered against six DFV of 5 M NaCl/50 mM TRIS pH 7.5 by use of a 0.05 µm hollow fiber (Spectrum): this is further called the high salt virus fraction.

Although the pore sizes of the hollow fiber (0.05 µm, about 800 kD) are large enough to allow passage of a 100 kD nucleoprotein, no nucleoprotein could be detected in the permeate and no reduction of the amount of nucleoprotein was seen in the retentate. Possibly, the adaptation of one or more TFF parameters (e.g., increase in shear) may improve purification of the nucleoprotein. Size exclusion (group separation) has been used to achieve this goal.

The high salt virus fraction was again split into two portions: one portion was directly purified and buffer exchanged to formulation buffer over a size exclusion (group separation) column (product B in FIG. 6), while the second fraction was stored overnight at room temperature before further purifying and buffer exchanging over a size exclusion (group separation) column (product C in FIG. 6).

The three purified bulk lots were analyzed to determine purity, infectivity, yield, aggregation and transgene expression.

Figure 7:
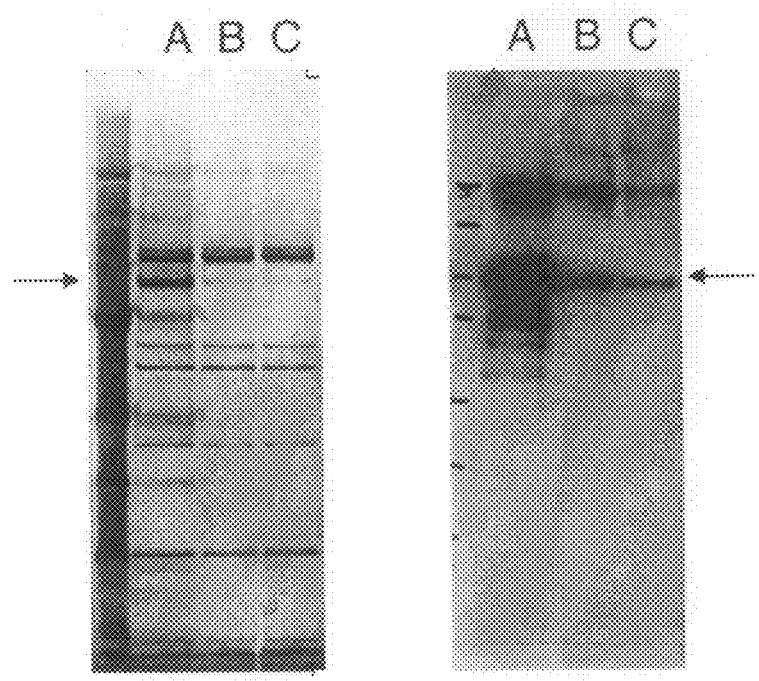

SDS-PAGE and Western analysis is shown in FIG. 7, and shows that the intact nucleoprotein, as well as NP degradation products (confirmed by mass spectrometry to be NP degradation products), are increasingly removed from products A, B and C, respectively.

Figure 8:
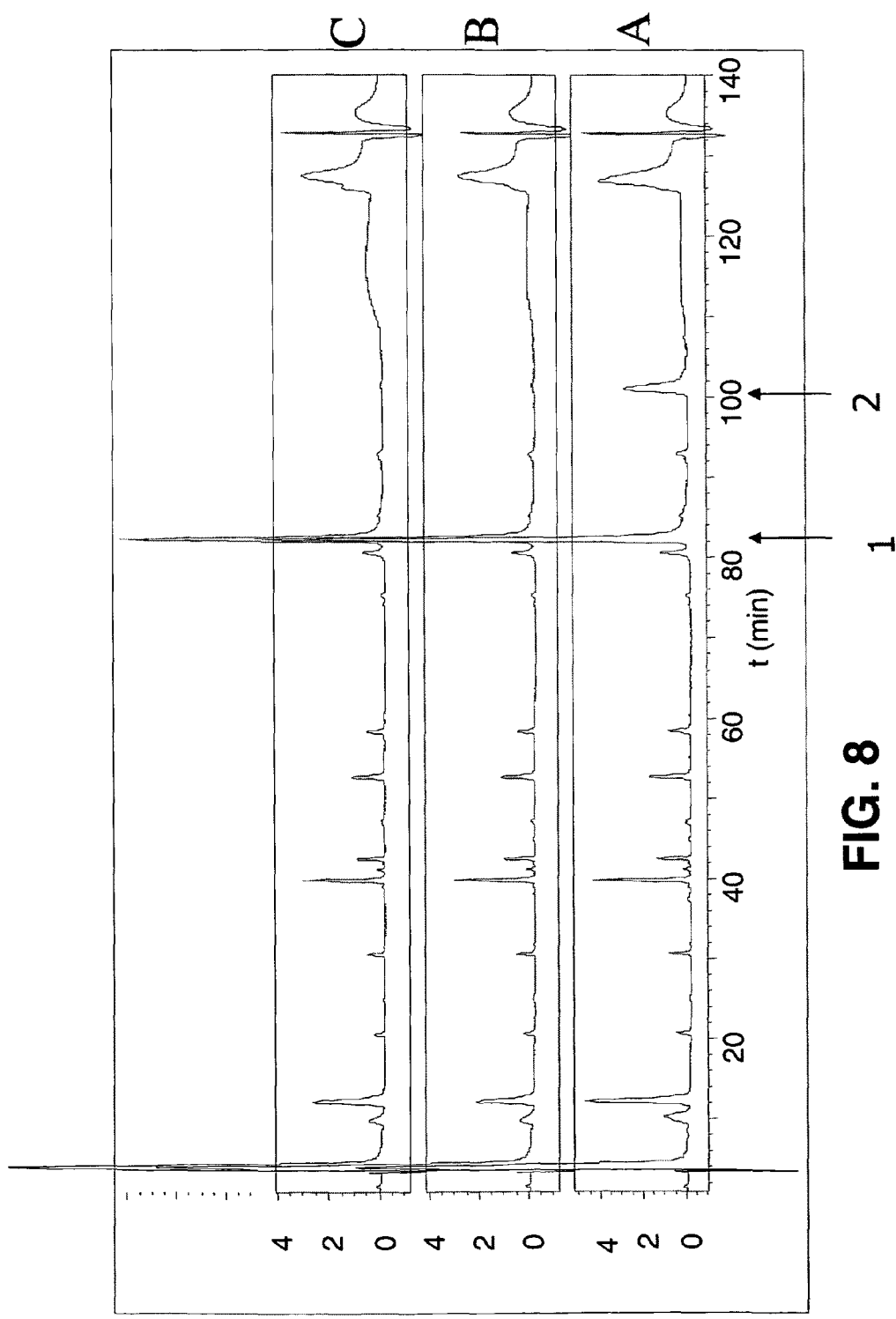

Reverse phase analysis (RP-HPLC) (FIG. 8) shows that the amount of intact nucleoprotein, as well as NP degradation product (eluting at 39 minutes), was reduced by introducing the high salt diafiltration step from about 50% (product A) to <5% (product B) and after overnight storage in 5 M NaCl at room temperature, even to below the detection limit of 1% (product C). Using both analysis methods, no effect on viral proteins was observed.

Transgene expression was shown, the infectivity was unaffected and no aggregation occurred (for all three products A, B and C). The incubation of the recombinant virus in high salt, even overnight, did not lead to a significant reduction in quality of the virus.

Instead of or in addition to prolonged incubation with high salt and subsequent size exclusion, a virus suspension that was buffer exchanged with 5M NaCl was directly filtered using a 0.45 µm hydrophilic filter (Millipac 20). Unexpectedly, this resulted in a complete removal of NP from the virus (FIG. 9). This experiment is repeated with filters of different pore sizes (e.g., 1.2, 1.0, 0.8, 0.22 µm) to determine the range of possible pore sizes. A 0.8/0.45 µm SARTOPORE® 2 combination is also tested. This filtration step may suitably be combined with a subsequent size exclusion chromatography step, and may require shorter incubation times of the virus in the high salt solution, resulting in a possible savings in process time.

Conclusions: 1. Diafiltration of the clarified harvest to 5 M NaCl is not feasible, probably due to precipitation of host cell proteins. 2. Incubation of highly purified Ad5dE3x.Adapt.Ebo.NP in 5 M NaCl followed by separation on Sepharose 4 FF or by filtration through a hydrophilic filter results in purification of Ad5dE3x.Adapt.Ebo.NP from the Ebola nucleoprotein. 3. Prolongation of the incubation step from two hours to overnight results in an even further reduction of residual nucleoprotein from <5% to <1%. Filtration through hydrophilic filters may reduce the required incubation time to obtain the same result.

Hence, it is feasible to remove nucleic acid binding proteins, such as nucleoproteins, e.g., nucleoprotein of Ebola virus, from recombinant viruses expressing such proteins, by incubation in at least 2 M NaCl, preferably at least 3 M NaCl, more preferably 5 M NaCl for purification purposes of batches of such viruses.

Example 4

Testing Different Filters for Clarification

PER.C6® cells were grown in a 10 L bioreactor and infected in separate experiments with different recombinant adenoviruses. Two and a half days after infection, the cells were lysed with 1% TRITON® X-100 and after 30 minutes, BENZONASE® (50 units/ml) and $MgCl_2$ were added and incubated for another 30 minutes. The harvest was used for clarification experiments.

Depth filters, e.g., Clarigard and Polygard, had high recovery (>90%) and good removal of cell debris (microscopic analysis), and were found suitable as an initial clarification filter. However the filtrate still looked opalescent.

Millistak DE 30/60 and CE50 were found to be less suitable for filtering T/B harvest due to loss of virus (20-45%). In later fractions, the yield increased but the retention of opalescence decreased, indicating that the filter capacity was reached.

Several membrane filters were tested to further clarify the filtrate produced by Clarigard filtration; e.g.: Milligard 0.5 µm, 1.2 µm and 1.2/0.22 µm, Durapore 0.22 and 0.65 µm, Lifegard 1.0 and 2.0 µm (all Millipore) and SARTOPORE® 2 0.8/0.45 µm (Sartorius). The SARTOPORE® 2 filter was the only filter among those tested that had a good retention of the opalescence, a high capacity (>20 ml/cm$^2$), as well as a high virus yield (>95%).

The clarified harvest was concentrated and diafiltrated with flatscreen or hollow fiber modules. Several filters were tested to filter the final retentate, preferably with a 0.45 µm pore size, in order to make the final retentate suitable for chromatography, e.g.: Millipack 20, Lifegard 1.0 µm, Polygard 0.6 µm, Intercept Q, Milligard 1.2/0.5 µm. Again, the SARTOPORE® 2 filter was the only filter among those tested that had a good retention of the opalescence, a high capacity, as well as a high virus yield (>95%).

Although these experiments were done with a T/B harvest, later experiments have confirmed the results above for a B/T harvest according to the invention and, hence, a SARTOPORE® 2 filter gives very good results with the methods according to the invention.

Hence, for the clarification in the methods according to the invention, preferably, a combination of 0.8 µm and 0.45 µm filters, preferably a Sartopore® 2 filter, is used.

Example 5

Generation and Purification of Different Recombinant Adenoviruses

Various recombinant adenoviruses were purified with methods according to the invention. Such viruses can, for instance, be generated by homologous recombination in the packaging cells of a left-end part (sometimes referred to as "adapter-plasmid," useful for easy cloning of the transgene) and a right-end part of the genome according to methods known from the art, such as described in EP 0955373, WO 03/104467 and WO 2004/001032, the contents of the entirety of each of which are incorporated herein by this reference. The viruses can be propagated in packaging cells known from the art, such as, 293 cells, PER.C6® cells (exemplified by cells deposited at the Centre for Applied Microbiology and Research Authority (European Collection of Animal Cell Cultures—ECACC), Porton Down, Salisbury, Wiltshire SP4, OJG, United Kingdom, an International Depository Authority, on Feb. 29, 1996 under deposit no. 96022940, see U.S. Pat. No. 5,994,128), or PER.E1B55K cells expressing E1B 55K protein from Ad35 (see, U.S. Pat. No. 6,492,169). Construction of some recombinant adenoviruses that were and are purified according to the methods of the invention is described in this example.

Adenovirus with Ebola Virus Transgenes
Generation of pAdapt.Ebola NP

The gene encoding the Ebola subtype Zaire nucleoprotein was amplified by polymerase chain reaction using primers; forward 6401 5' GCA CCG GTG CCG CCA TGG ATT CTC GTC CTC A 3' (SEQ ID NO: 1) and reverse 6401 5' GCG CTA GCT CAC TGA TGA TGT TGC AG 3' (SEQ ID NO: 2) in order to introduce restriction endonuclease recognition sites and a consensus sequence for optimal translation initiation (M. Kozak, 1987, "At least six nucleotides preceding the AUG initiator codon enhance translation in mammalian cells," J. Mol. Biol. 20: 947-950) for directional cloning in pAdApt™ (see, EP 0955373). PCR reactions were performed in a Biometra T1 or T3 thermal cycler using 10 µM of each primer, 0.75 µl miniprep DNA of VRC6401 (see, WO 03/028632), 1.5 units Pwo DNA polymerase, 5 µl 10×PCR buffer, 0.5 µl 20 mM dNTPs using the following conditions: one cycle of five minutes at 94° C., one minute at 50° C., and four minutes at 72° C.; five cycles of one minutes at 94° C., one minute at 50° C., and four minutes at 72° C.; 20 cycles of one minute at 94° C., one minute at 62° C., and four minutes at 72° C.; one cycle of one minute at 94° C., one minute at 62° C., and ten minutes at 72° C. Subsequently, the PCR product of the correct size was digested with PinAI (Isoschizomer of AgeI) and ligated into the pAdApt™ vector digested with PinAI and HpaI. After ligating the fragment for two hours at room temperature, 50% of the mixture was transformed to E. coli DH5α T1R cells by heatshock transformation and plated onto LB agar plates supplemented with 50 µg/ml ampicillin. Twenty colonies were picked and grown overnight at 37° C. in LB supplemented with ampicillin. Miniprep DNA was extracted using the Qiagen miniprep Spin kit as described by the manufacturer. After restriction enzyme analysis with HindIII and XbaI, a correct clone was selected and further checked by DNA sequence analysis.

Generation of pAdapt.Ebola GP (Z)

The gene encoding the Ebola subtype Zaire full-length glycoprotein was amplified by PCR using primers Forward 6001 (5' CCC AAG CTT GCC GCC ATG GGC GTT ACA GG 3') (SEQ ID NO: 3) and Reverse 6001 (5' GGC TCT AGA TTA CTA AAA GAC AAA TTT GC 3') (SEQ ID NO: 4). PCR reactions were performed in a Biometra T1 or T3 thermal cycler using 10 µM of each primer, 100 ng and 25 ng DNA of VRC6001 (see, WO 03/028632), 1.5 units Pwo DNA polymerase, 5 µl 10×PCR buffer, 0.5 µl 20 mM dNTPs using the following conditions: one cycle of five minutes at 94° C., one minute at 55° C., and four minutes at 72° C.; five cycles of one minute at 94° C., one minute at 55° C., and four minutes at 72° C.; 20 cycles of one minute at 94° C., one minute at 64° C., and four minutes at 72° C.; one cycle of one minute at 94° C., one minute at 64° C., and ten minutes at 72° C. Subsequently, the PCR product of the correct size was digested with HindIII and XbaI and ligated into the likewise digested pAdApt™ vector. After ligating the fragment for two hours at room temperature, 50% of the mixture was transformed to E. coli DH5α T1R cells by heatshock transformation and plated onto LB agar plates supplemented with 50 µg/ml ampicillin. Colonies were picked and grown overnight at 37° C. in LB supplemented with ampicillin. Miniprep DNA was extracted using the Qiagen miniprep Spin kit as described by the manufacturer. After restriction enzyme analysis with HindIII and XbaI, correct clones were selected and further checked by DNA sequence analysis.

Generation of pAdapt.Ebola GPdTM(Z) and pAdapt.Ebola GPdTM(S)

Similarly as described above, codon-optimized sequences encoding one of the Ebola subtypes Zaire and Sudan/Gulu glycoprotein with a deletion of the C-terminal 29 amino acids long transmembrane domain (GPdTM(Z), and GPdTM(S), respectively, see also WO 03/028632), were cloned into pAdapt.

Generation of Recombinant Adenoviruses with Ebola Virus Transgenes

The pAdapt plasmids with the different inserts (pAdapt.Ebola NP, pAdapt.Ebola GP (Z), pAdapt.Ebola GPdTM (S), pAdapt.Ebola GPdTM (Z)), were used to form recombinant adenoviruses by homologous recombination with plasmids comprising the remainder of the adenovirus type 5 genome (plasmid pWE/Ad.AflII-rITRspΔE3, which is pWE/Ad.AflII-rITRsp (see, EP 0955373) with a deletion of 1878 bp in the E3 region (XbaI region) was used for the right end of the adenovirus genome), according to well known methods such as described in EP 0955373, resulting in viruses named Ad5dE3x.Adapt.Ebo.NP, Ad5dE3x.Adapt.Ebo.GP(Z), Ad5dE3x.Adapt.Ebo.GPdTM(S) and Ad5dE3x.Adapt.Ebo.GPdTM(Z), respectively. The transgenes can similarly be cloned in adenovirus vectors of different serotypes, such as Ad35, to generate recombinant adenovirus derived from those serotypes (see, e.g., WO 00/70071).

Adenoviruses with *Plasmodium* Transgene
Generation of pAdapt.CSpFalc and pAdapt535.CS.Pfalc A codon-optimized circumsporozoite (CS) gene of *Plasmodium falciparum* was synthesized and cloned into pCR-script (Stratagene), giving clone 02-659, as described in WO 2004/055187. The CS gene was cloned into pAdapt and pAdapt535 (see, WO 2004/001032) for generation of recombinant Ad5 and recombinant Ad35 vectors, respectively. Clone 02-659 and both pAdapt vectors were digested with HindIII and BamHI and joined by ligation. After ligating the fragment for two hours at room temperature, 50% of the mixture was transformed to E. coli DH5α T1R cells by heat shock transformation and plated onto LB agar plates supplemented with 50 µg/ml ampicillin. Colonies were picked and grown overnight at 37° C. in LB supplemented with ampicillin. Miniprep DNA was extracted using the Qiagen miniprep Spin kit. After restriction enzyme analysis with HindIII and XbaI, correct clones were selected and further checked by DNA sequence analysis.

Recombinant adenovirus serotype 5 with the *P. falciparum* CS gene was generated as follows (see, for instance, EP 0955373; also described in WO 2004/055187). pAdapt.CS.Pfalc was digested by PacI restriction enzyme to release the left-end portion of the Ad genome. Plasmid pWE/Ad.AflII-rITRspΔE3 containing the right-end part of the Ad5 genome has a deletion of 1878 bp in the E3 region (XbaI deletion), and was also digested with PacI. The digested constructs were co-transfected into PER.C6® cells, such as deposited at the ECACC under number 96022940. Upon homologous recombination of the overlapping sequences, recombinant virus named Ad5ΔE3.CS.Pfalc was formed.

Recombinant adenovirus serotype 35 with the *P. falciparum* CS gene was generated similarly, but now PacI-digested pAdapt535.CS.Pfalc was used for the left-end of the virus genome, and NotI-digested pWE.Ad35.pIX-rITRΔE3 (see, WO 2004/001032) was used for the right-end of the virus genome, and both were transfected into PER-E1B55K producer cells (having E1B-55K sequences derived from Ad35; cells have been described in U.S. Pat. No. 6,492,169). Upon homologous recombination of the overlapping sequences, recombinant virus named Ad35ΔE3.CS.Pfalc was formed. It would also be possible to change the E4-orf6 protein in the backbone of the Ad35 virus into E4-orf6 of Ad5 to render it possible to propagate such viruses on packaging cells that express the E1B protein of Ad5, such as PER.C6® or 293 cells (see, WO 03/104467).

Ad5ΔE3.CS.Pfalc and Ad35ΔE3.CS.Pfalc are purified according to the methods of the invention.

In addition, an Ad35 vector with the CS gene, based on pAdapt535.CS.Pfalc with an Ad35 backbone, was constructed, having a deletion in E3 and further comprising E4-orf6 of Ad5: this vector is further referred to as Ad35.CS.

Several Adenovirus vectors were purified with the described process (example 1, FIG. 4): Ad5dE3x.Adapt.Ebo.GPdTM(Z); Ad5dE3x.Adapt.Ebo.GPdTM(S); Ad5dE3x.Adapt.Ebo.NP, and Ad5dE3x.Adapt.Empty on a 2 to 20 L scale. The filled and finished (F&F) products were analyzed for purity by reverse phase and SDS-PAGE and found to be purified near homogeneity (except for the presence of the Ebola nucleoprotein in the preparations of the vectors having Ebola nucleoprotein as a transgene). The amount of residual host cell DNA was measured by Q-PCR and was below 100 pg DNA/ 1E11 VP (as shown in Table 1).

Aggregation was measured by optical density measurements at 320 and 260 nm, and also by disc centrifugation. None of the batches showed aggregation. Potency was shown in all batches by a VP/IU ratio below 10, and transgene expression was shown in A549 cells.

The final yield ranged from 20-50% dependent on the scale: 2 L: 24-26% (n=2); 10 L: 30-37% (n=3); 20 L: 46% (n=1).

Example 6

Ad35 Purification Using Anion Exchange Chromatography Versus Charged Filters

PER.C6® cells were grown in a stirred tank to cell density of about 1 million cells/ml. The cells were infected with the Ad35.CS vector with a MOI of 40. After four days of virus production, the infected cell culture was treated with BENZONASE® and TRITON® X-100 (B/T method) as described in Example 1. The B/T harvest was clarified as described in Example 1. The clarified harvest was concentrated five times by TFF (using a 0.05 μm hollow fiber), and subsequently diafiltered against ten diafiltration volumes of 0.1 M NaCl, 0.05% PS80, 50 mM Tris pH 7.5. The concentrated and diafiltered retentate was filtered over a 0.45 μm filter and loaded onto the capturing column or filter. As a capture step, a Q-XL column (3 ml column, 15 cm bed height) or a Sartobind 75 filter (charged filter containing anionic groups, Sartorius) were tested. The bound components were eluted with a gradient from 0 to 1 M NaCl in a TRIS-based buffer. The elution profile of the charged filter shows an extra peak at the beginning of the gradient, which is separated from the Ad35 peak. The Ad35 virus peak elutes from the charged filter in a sharper peak at a higher salt concentration, 0.44 M NaCl (start 0.41, end 0.49 M NaCl) compared to the Q-XL resin, 0.39 M NaCl (start 0.19, end 0.53 M NaCl). The eluted fractions were analyzed by SDS-PAGE, HPLC-AEX, disc centrifugation and TCID50.

Figure 11:
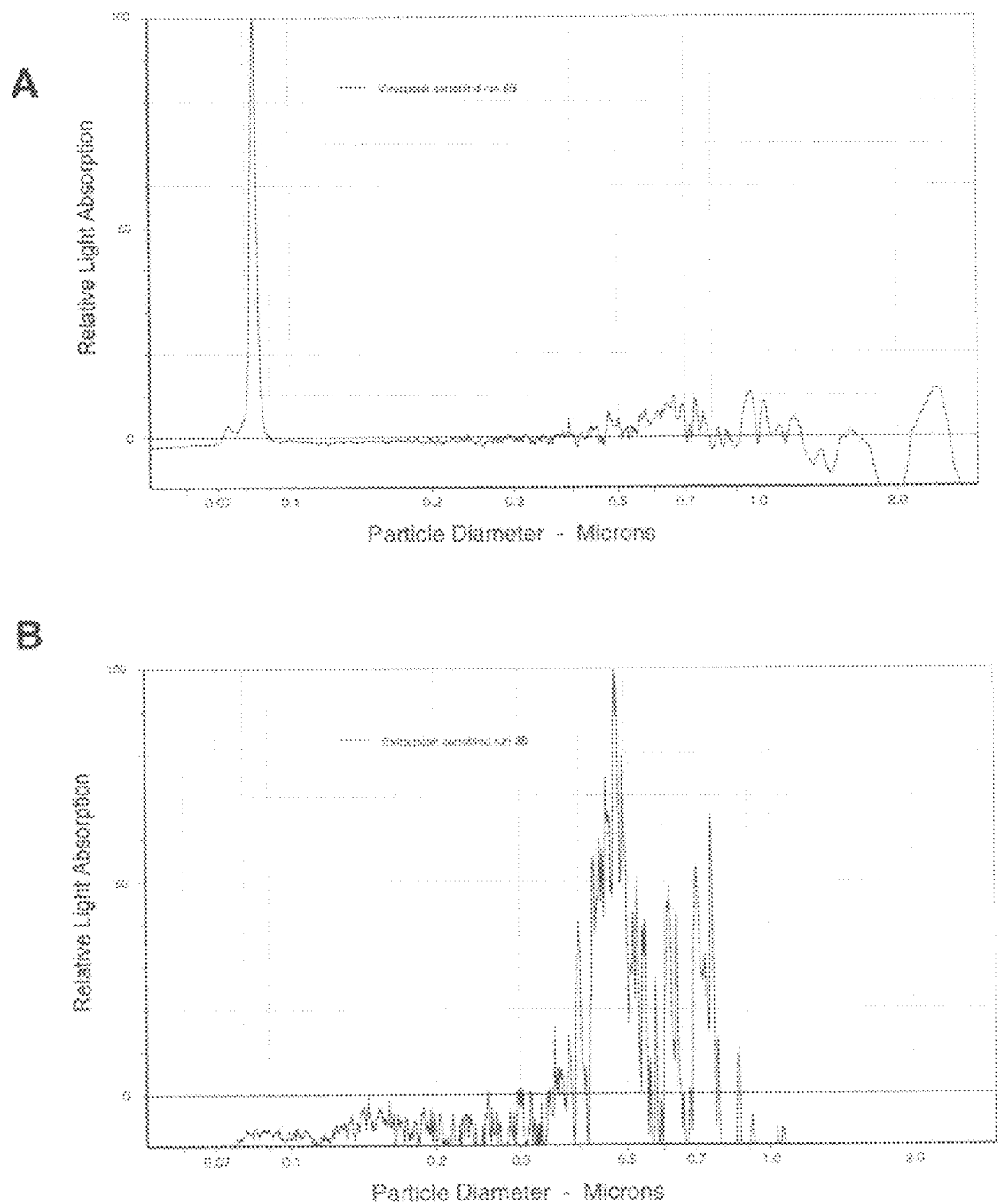
Figure 12:
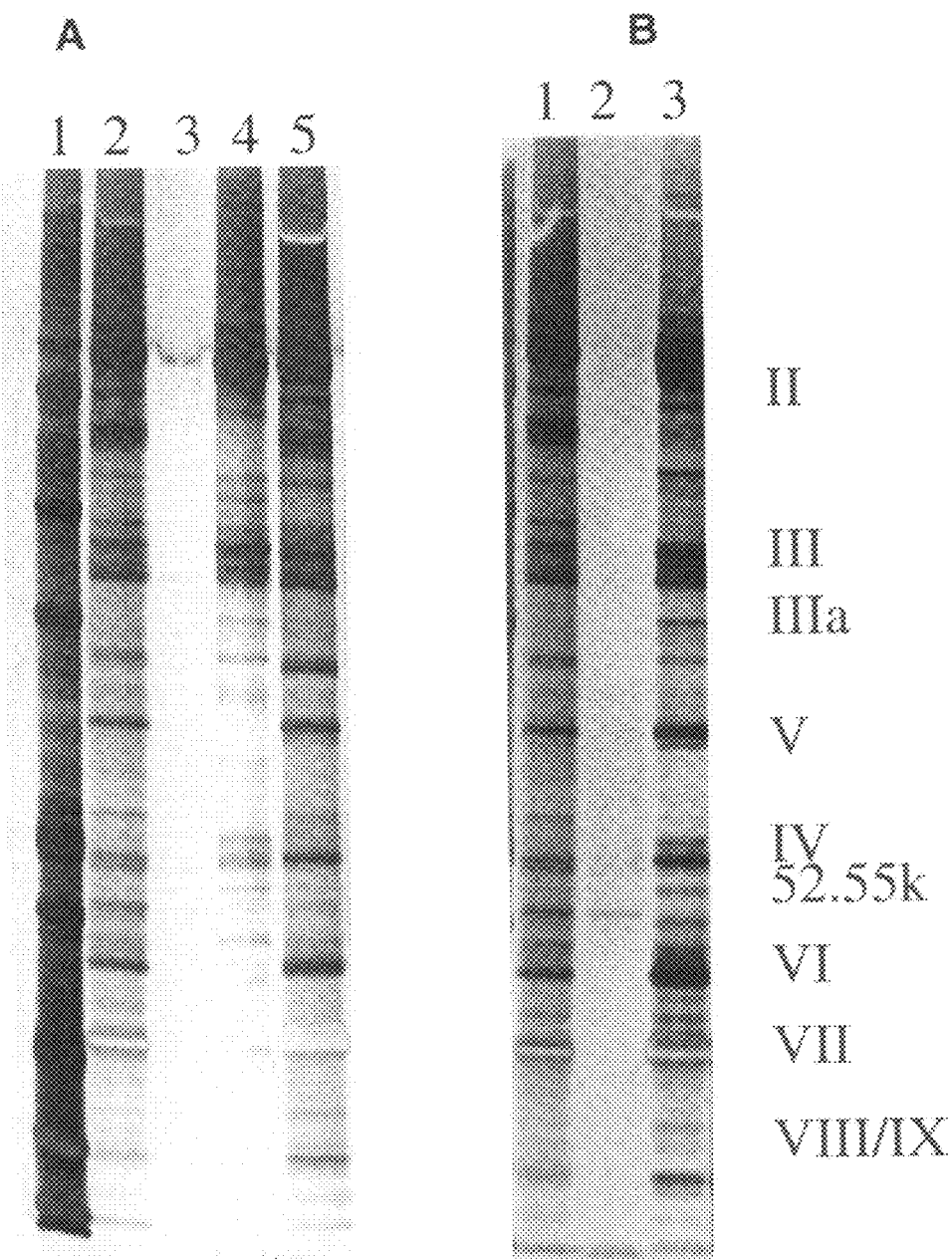

The extra peak does not behave as intact Ad35 virus particles when analyzed by HPLC-AEX chromatography and disc centrifugation (FIG. 11). SDS-PAGE analysis of the chromatography fractions shows the following results (FIG. 12): In the flow through of both runs, no or very low amounts of proteins are visible. The extra peak from the charged filter chromatogram shows some but not all Ad35 proteins. In the extra peak, viral proteins IIIa, V, VI and VII appear to be missing, while viral proteins II, III, IV and 52.55 k are present.

From these analysis data, it can be concluded that charged filters can separate viral proteins from intact viral particles, while Q-XL sepharose cannot. If no separation occurs, this will most likely not be detected by assays to assess purity like RP-HPLC or SDS-PAGE, since all proteins present in the extra peak are also present in the intact virion.

TABLE 1

Reduction of the amount of residual host cell DNA in purified bulk samples by reversing the T/B to a B/T harvest method. The harvest was purified on a 2-20 L scale. See example 1 for details.

| Run | Vector | harvest method | Host Cell DNA ng/ml | VP/ml HPLC-AEX | ng HC DNA/ 1E11 VP |
|---|---|---|---|---|---|
| 1 | Ad5.MV-H | T/B | 0.41 | 5.40E+10 | 0.78 |
| 2 | Ad5dE3x.Adapt.Ebo.GPdTM (Z) | T/B | 4.31 | 5.25E+11 | 0.82 |
| 3 | Ad5dE3x.Adapt.Ebo.NP | B/T | 0.46 | 7.80E+11 | 0.06 |
| 4 | Ad5dE3x.Adapt.Ebo.NP | B/T | 0.44 | 6.80E+11 | 0.07 |
| 5 | Ad5dE3x.Adapt.Empty | B/T | 0.40 | 8.90E+11 | 0.04 |
| 6 | Ad5dE3x.Adapt.Ebo.NP | B/T | 0.25 | 4.66E+11 | 0.05 |
| 7 | Ad5dE3x.Adapt.Ebo.GPdTM (S) | B/T | 0.55 | 6.60E+11 | 0.08 |
| 8 | Ad5dE3x.Adapt.Ebo.GPdTM (Z) | B/T | 0.15 | 6.60E+11 | 0.02 |
| 9 | Ad353.CS | B/T | 0.62 | 5.15E+11 | 0.12 |

TABLE 2

NP removal at different ionic strength and after different incubation times. See example 3 for details.

|  | 2 hours | Overnight |
|---|---|---|
| 1 M NaCl | − | − |
| 2 M NaCl | − | + |
| 3 M NaCl | +/− | + |
| 5 M NaCl | + | ++ |

What is claimed is:

1. A method for removing adenovirus proteins that are not incorporated into subgroup B recombinant human adenovirus particles from a preparation of subgroup B recombinant human adenovirus particles, the method comprising the steps of:

subjecting a preparation of the recombinant adenovirus particles comprising adenovirus proteins that are not incorporated into adenovirus particles to a charged filter that contains anion exchange groups, wherein the preparation of the recombinant adenovirus particles comprises subgroup B recombinant human adenovirus particles thus removing adenovirus proteins that are not incorporated into the adenovirus particles, said adenovirus proteins comprising subgroup B adenoviral proteins II, III, IV, and 52.55 k; and analyzing the filtered preparation to determine whether subgroup B adenoviral 52.55 k protein that is not incorporated into adenovirus particles has been removed from the preparation.

2. The method according to claim 1, wherein the recombinant adenovirus is an Ad35 recombinant adenovirus.

3. A method for purifying a preparation of subgroup B recombinant human adenovirus particles, wherein proteins comprising subgroup B adenoviral proteins II, III, IV, and 52.55 k not incorporated into the recombinant adenovirus particles are to be removed, the method comprising:

analyzing the filtered preparation to determine whether subgroup B adenoviral protein 52.55 k has been removed from the preparation, said preparation having been previously subjected to a charged filter containing anion exchange groups.

4. A method for removing adenovirus proteins II, III, IV, and 52.55 k that are not incorporated into adenovirus particles from a preparation of subgroup B recombinant human adenovirus particles, the method comprising:

subjecting a preparation of subgroup B recombinant human adenovirus particles to a charged filter that contains anion exchange groups; thus separating and removing the adenovirus proteins II, III, IV, and 52.55 k that are not incorporated into adenovirus particles from the preparation of subgroup B recombinant human adenovirus particles, and analyzing the filtered preparation to determine removal of adenoviral proteins that have not been incorporated into adenovirus particles from the preparation.

5. The method of claim 3, wherein the adenovirus is an Ad35 recombinant adenovirus.

6. The method of claim 4, wherein the adenovirus is an Ad35 recombinant adenovirus.

* * * * *

SEQUENCE LISTING

<160> NUMBER OF SEQ ID NOS: 4

<210> SEQ ID NO 1
<211> LENGTH: 31
<212> TYPE: DNA
<213> ORGANISM: Artificial
<220> FEATURE:
<223> OTHER INFORMATION: primer forward 6401

<400> SEQUENCE: 1
gcaccggtgc cgccatggat tctcgtcctc a                           31

<210> SEQ ID NO 2
<211> LENGTH: 26
<212> TYPE: DNA
<213> ORGANISM: Artificial
<220> FEATURE:
<223> OTHER INFORMATION: primer reverse 6401

<400> SEQUENCE: 2
gcgctagctc actgatgatg ttgcag                                 26

<210> SEQ ID NO 3
<211> LENGTH: 29
<212> TYPE: DNA
<213> ORGANISM: Artificial
<220> FEATURE:
<223> OTHER INFORMATION: primer forward 6001

<400> SEQUENCE: 3
cccaagcttg ccgccatggg cgttacagg                              29

<210> SEQ ID NO 4
<211> LENGTH: 29
<212> TYPE: DNA
<213> ORGANISM: Artificial
<220> FEATURE:
<223> OTHER INFORMATION: primer reverse 6001

<400> SEQUENCE: 4
ggctctagat tactaaaaga caaatttgc                              29